(12) United States Patent
Church et al.

(10) Patent No.: US 7,985,546 B2
(45) Date of Patent: Jul. 26, 2011

(54) GENOMIC LIBRARY CONSTRUCTION

(75) Inventors: George M. Church, Brookline, MA (US); Kun Zhang, San Diego, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 12/265,184

(22) Filed: Nov. 5, 2008

(65) Prior Publication Data

US 2009/0137407 A1 May 28, 2009

Related U.S. Application Data

(63) Continuation of application No. PCT/US2007/012229, filed on May 18, 2007.

(60) Provisional application No. 60/801,340, filed on May 18, 2006.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.33

(58) Field of Classification Search ............ 435/6, 91–2; 536/24.33
See application file for complete search history.

(56) References Cited

U.S. PATENT DOCUMENTS

| | | | |
|---|---|---|---|
| 5,811,239 A | 9/1998 | Frayne | |
| 6,617,137 B2 | 9/2003 | Dean et al. | |
| 2004/0209298 A1* | 10/2004 | Kamberov et al. | 435/6 |
| 2006/0014167 A1 | 1/2006 | Church et al. | |
| 2009/0215034 A1* | 8/2009 | Maes et al. | 435/6 |

OTHER PUBLICATIONS

Frank B. Dean, Seiyu Hosono, Linhua Fang, Xiaohong Wu, A. Fawad Faruqi, Patricia Bray-Ward, Zhenyu Sun, Qiuling Zong, Yuefen Du, Jing Du, Mark Driscoll, Wanmin Song, Stephen F. Kingsmore, Michael Egholm and Roger S. Lasken. Comprehensive human genome amplification using multiple displacement amplification, PNAS, Apr. 16, 2002, vol. 99 No. 8, pp. 5261-5266.

Lin Zhang, Xiangfeng Cui, Karin Schmitt, Rene Hubert, William Navidi, and Norman Arnheim. Whole genome amplification from a single cell: Implications for genetic analysis, Proc. Natl. Acad. Sci USA, Jul. 1992, vol. 89, pp. 5847-5851.

G. Terrance Walker, Michael C. Little, James G. Nadeau and Daryl D. Shank. Isothermal in vitro amplification of DNA by a restriction enzyme/DNA polymerase system, Proc. Natl. Acad. Sci. USA, Jan. 1992, vol. 89, pp. 392-396.

Janelle R. Thompson, Sarah Pacocha, Chanathip Pharino, Vanja Klepac-Ceraj, Dana E. Hunt, Jennifer Benoit, Ramahi Sarma-Rupavtarm, Daniel L. Distel, Martin F. Polz. Genotypic Diversity Within a Natural Coastal Bacterioplankton Population, (2005) Science 307:1311-1313.

Jay Shendure, Gregory J. Porreca, Nikos B. Reppas, Xiaoxia Lin, John P. McCutcheon, Abraham M. Rosenbaum, Michael D. Wang, Kun Zhang, Robi D. Mitra, George M. Church. Accurate Multiplex Polony Sequencing of an Evolved Bacterial Genome, (2005) Science 309: 1728-1732.

Clyde A. Hutchison III, Hamilton O. Smith, Cynthia Pfannkoch and J. Craig Venter. Cell-free cloning using Phi29 DNA polymerase, (Nov. 29, 2005) PNAS, vol. 102 No. 48: 17332-17336.

Shendure et al. (2004) Nature Review Genetics 5:335.
Telenius et al. (1992) Genomics 13:718.
Dietmaier et al. (1999) Am J. Pathol. 154:83.
Nelson et al. (2002) Biotechniques Suppl:44.
Lage et al. (2003) Genome Res. 13:294.
Handyside et al. (2004) Mol. Hum. Reprod. 10:767.
Hellani (2004) Mol. Hum. Reprod. 10:847.
Sorenson (2004) Anal. Biochem. 324:312.
Detter et al. (2002) Genomics 80:691.
Raghunathan et al. (2005) Appl. Environ. Microbiol. 71:3342.
Hafner et al. (2001) Biotechniques 30:852.
Lizardi et al. (1998) Natl. Genet. 19:225.
Hosono et al. (2003) Genome Res. 13:954.
Paez et al. (2004) Nucleic Acids Res. 32:, No. 9, e71.
Panelli et al. (2005) Biotechniques 39:174.
Margulies et al. (2005) Nature 437:376.
Acinas et al. (2004) Nature 430:551.
International Search Report relating to corresponding PCT/US07/12229.
Written Opinion relating to corresponding PCT/US07/12229.

* cited by examiner

*Primary Examiner* — Suryaprabha Chunduru
(74) *Attorney, Agent, or Firm* — Banner & Witcoff, Ltd.

(57) ABSTRACT

Compositions and methods for amplifying nucleic acid sequences from a single cell are provided. Compositions and methods for constructing a genomic library from a single cell are also provided.

24 Claims, 18 Drawing Sheets
(17 of 18 Drawing Sheet(s) Filed in Color)

8A

8B 12A
12B

14A

14B

GENOMIC LIBRARY CONSTRUCTION

RELATED U.S. APPLICATIONS

This application is a continuation of PCT application no. PCT/US2007/012229, designating the United States and filed May 18, 2007; which claims the benefit of the filing date of U.S. Provisional Patent Application No. 60/801,340, filed on May 18, 2006, each of which is hereby incorporated herein by reference in its entirety for all purposes.

STATEMENT OF GOVERNMENT INTERESTS

This application was funded in part by grant number DE-FG02-02ER63445 from the United States Department of Energy. The Government has certain rights in the invention.

FIELD OF THE INVENTION

The present invention relates to methods of amplifying nucleic acids from single cells and methods of constructing genomic libraries from single cells.

BACKGROUND OF THE INVENTION

Over the past two decades, the power of DNA sequencing has increased exponentially (Shendure et al. (2004) *Nature Review Genetics* 5:335, incorporated herein by reference in its entirety for all purposes), leading to the sequencing of the genomes of over 355 organisms (Kyrpides (1999) *Bioinformatics* 15:773, incorporated herein by reference in its entirety for all purposes). Nevertheless, much of the genetic diversity of the biosphere remains unsampled (Moreira and Lopez-Garcia (2002) *Trends Microbiol.* 10:31; Falkowski and de Vargas (2004) *Science* 304:58, each of which is incorporated herein by reference in its entirety for all purposes). Most of this diversity is due to microorganisms which cannot be easily cultured as large clonal pools required for conventional genome sequencing.

Metagenomic approaches that do not require such culturing, such as environmental shotgun sequencing and large insert library sequencing, while revealing the enormous biodiversity in environmental samples, suffer from two major drawbacks: (1) the difficulty of assembling contigs into discrete genomes, and (2) biased sampling toward abundant species (Tyson et al. (2004) *Nature* 428:37; Venter et al. (2004) *Science* 304:66; DeLong (2005) *Nat. Rev. Microbiol.* 3:459; Beja et al. (2002) *Appl. Environ. Microbiol.* 68:335; Tringe et al. (2005) *Science* 308:554; Riesenfeld et al. (2004) *Ann. Rev. Genet.* 38:525; Rodriguez-Valera (2004) *FEMS Microbiol. Lett.* 231:153, each of which is incorporated herein by reference in its entirety).

Isothermal multiple displacement amplification (MDA) is superior to PCR based methods in terms of high-yield, high-fidelity, and a lack of significant bias in terms of sequence coverage, but is known to yield a dominant "background" of undesired amplification when template drops below nanogram levels (Dean et al. (2002) *Proc. Natl. Acad. Sci. U.S.A.* 99:5261; Telenius et al. (1992) *Genomics* 13:718; Zhang et al. (1992) *Proc. Natl. Acad. Sci. U.S.A.* 89:5847; Dietmaier et al. (1999) *Am. J. Pathol.* 154:83; Nelson et al. (2002) *Biotechniques Suppl.*:44; Lage et al. (2003) *Genome Res.* 13:294, each of which is incorporated herein by reference in its entirety). Accordingly, mixed results have been reported on such amplifications from single human cells (Handyside et al. (2004) *Mol. Hum. Reprod.* 10:767; Hellani (2004) *Mol. Hum. Reprod.* 10:847; Sorensen (2004) *Anal Biochem.* 324:312, each of which is incorporated herein by reference in its entirety).

Microorganisms with smaller genomes pose an even greater challenge as the mass of a single genome is typically at the femtogram level, while the standard MDA protocol requires from about one to about ten nanograms of template DNA (Dean et al., supra, incorporated herein by reference in its entirety for all purposes). Genome sequencing of *Xylella fastidiosa* was only possible when amplified with MDA from approximately 1000 cells (Detter et al. (2002) *Genomics* 80:691, incorporated herein by reference in its entirety for all purposes). Although initial success has been reported on genome amplification from single *E. coli* cells, it has been estimated that only 30% of amplified DNA was specific to the target genome due to the presence of background amplification (Raghunathan et al. (2005) *Appl. Environ. Microbiol.* 71:3342, incorporated herein by reference in its entirety for all purposes). Reduction of reaction volume offers a way to reduce background amplification (Hutchison et al. (2005) *Proc. Natl. Acad. Sci. U.S.A.* 102:17332, incorporated herein by reference in its entirety for all purposes). However, to bridge these methods to single cell genome sequencing, a number of critical technical issues remain to be addressed, such as the quantification of background, amplification bias, amplification error, and the compatibility to current genome sequencing pipelines.

The ability to sequence an entire genome from a single uncultured cell opens a window to genomic information not evident with current metagenomic or population-based methods. Such an ability is highly desirable for charting the largely unmapped genomic biosphere, allowing genomic analyses not feasible with current methods such as: (1) the characterization of genetic heterogeneity in a population of cells; (2) the revelation of cis-relationship between sequences greater than 200 kb apart (unreachable by BAC/fosmid cloning); (3) the study of trans-interactions between host and parasitic genomes (phages and viral) or cell-cell interactions (e.g., predator-prey, symbionts, commensals); and/or (4) the identification of rare species for genome sequencing. Such an ability is highly desirable for charting the largely unmapped genomic biosphere.

SUMMARY OF THE INVENTION

The present invention is based in part on the discovery of a novel method to amplify nucleic acid sequences from small samples of genetic material, e.g., genetic material from single cells. Embodiments of the present invention are directed to a method of amplifying nucleic acid sequences, e.g., genomic sequences, from a single cell including the steps of amplifying a nucleic acid sequence, and contacting the amplified nucleic acid sequence with enzymes that remove hyperbranched DNA structures and/or repair nicks in an amplified nucleic acid sequence.

In certain aspects of the invention, phi-29 DNA polymerase and/or S1 nuclease are used to reduce the presence of hyperbranched DNA in an amplified DNA sequence. In other aspects of the invention, DNA polymerase I is used to repair nicks in an amplified DNA sequence. In other aspects, enzymes are added to reduce the presence of hyperbranched DNA in the following order: phi-29 DNA polymerase; S1 nuclease; and DNA polymerase I. In certain aspects, genomic DNA is amplified. In other aspects, amplification is performed using multiple displacement amplification.

Further embodiments of the present invention are directed to a method of reducing hyperbranched nucleic acid sequences present in an amplified nucleic acid sequence from a single cell by amplifying a nucleic acid sequence from the single cell, and contacting the amplified nucleic acid sequence with phi-29 DNA polymerase, S1 nuclease and DNA polymerase I.

Other embodiments of the present invention are directed to a method of reducing chimeric nucleic acid sequences in cloned DNA by amplifying a nucleic acid sequence, contacting the amplified nucleic acid sequence with phi-29 DNA polymerase, S1 nuclease and DNA polymerase I, placing the amplified DNA into a vector, and cloning the vector.

Embodiments of the present invention are also directed to a method of constructing a genomic library by obtaining genomic DNA from a single cell, amplifying the genomic DNA to produce amplified genomic DNA, contacting the amplified genomic DNA with phi-29 DNA polymerase, S1 nuclease and DNA polymerase I, placing said amplified genomic DNA into two or more vectors, and transforming the vectors into competent cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which.

DETAILED DESCRIPTION

Figure 1:
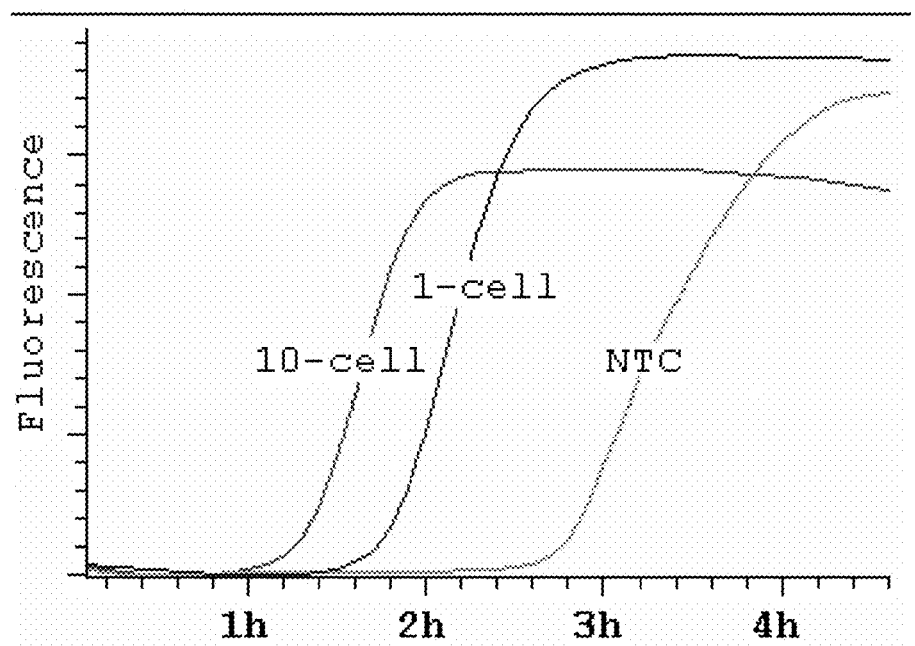
FIG. 1 depicts ploning on *E. coli* single cells. The genome of single *E. coli* cells was successfully amplified when the background was suppressed to a sub-femtogram level. The amplification curves from one cell and from no-template control (NTC) were well-separated, indicating background amplification did not interfere with template-specific amplification. The ten cell amplification was conducted on one μl of *E. coli* cells diluted at the ten cell/μl level. The number of cells in the one cell dilution was confirmed as described in the Examples. Strain-specific amplification showed that both plones were amplified from single cells of the NR57 strain.

The principles of the present invention may be applied with particular advantage to amplify nucleic acids from pools containing small amounts of template nucleic acid, e.g., nucleic acid sequences from single cells, e.g., single cell genomes. The present invention presents a novel method of overcoming the generation of hyperbranched nucleic acid, e.g., hyperbranched DNA, when amplifying small amounts of DNA using amplification methods known in the art, such as isothermal amplification.

Embodiments of the present invention are directed to the use of strand displacement amplification (SDA) to amplify nucleic acid sequences. SDA is an isothermal, in vitro method of amplifying DNA. A variety of SDA methods are described in the art including multiple displacement amplification (MDA) (Walker et al. (1992) *Proc. Natl. Acad. Sci. U.S.A.* 20:1691; Dean et al., (2002) *Proc. Natl. Acad. Sci. U.S.A.* 99:5261; Hafner et al. (2001) *Biotechniques* 30:852; Lizardi et al. (1998) *Nat. Genet.* 19:225; U.S. patent application Ser. No. 11/066,559, filed Feb. 28, 2005, each of which is incorporated herein by reference in its entirety for all purposes). The use of SDA (e.g., MDA) to amplify small amounts of nucleic acid sequences e.g., genomic DNA from a single cell, often leads to the generation of many undesirable hyperbranched DNA sequences. The presence of such hyperbranched DNA results in the formation of undesired chimeric sequences in cloned DNA.

Embodiments of the present invention are directed to methods of reducing hyperbranched nucleic acid sequences, e.g., hyperbranched DNA. As used herein, the term "hyperbranched DNA" is intended to include, but is not limited to, an amplified DNA sequence having regions containing one or more copies of a portion of the original DNA. Hyperbranched DNA can contain both double-stranded sequences as well as overhanging single stranded sequences. For a review of hyperbranched DNA, see Lage et al. ((2003) *Genomic Res.* 13:294, incorporated herein by reference in its entirety for all purposes).

Certain embodiments of the present invention are directed to methods of decreasing the frequency of chimeric sequences in amplified nucleic acid sequences. As used herein, the term "chimeric sequence" is intended to include, but is not limited to, a nucleic acid sequence that contains native sequence as well as non-native sequence and/or a nucleic acid sequence containing repeated regions of native sequence.

In certain embodiments of the invention, the presence of hyperbranched DNA may be reduced using an enzyme, e.g., a polymerase, that reduces the density of branch junctions (i.e., of hyperbranched sequences) in the amplified nucleic acid pool. In certain aspects of the present invention, one or more polymerases having a strand-replacement activity are contacted to an amplified nucleic acid pool (during or after amplification) in order to reduce the presence of branching junctions in the amplified nucleic acid pool. Suitable polymerases include, but are not limited to, polymerases having a strand displacement activity such as phi-29 DNA polymerase, bacteriophage T5 DNA polymerase, vent DNA polymerase, Bst DNA polymerase, THERMOPHI™ DNA polymerase (Prokaria, Reykjavik, Iceland), TOPOTAQ™ DNA polymerase (Fidelity Systems, USA), Tli DNA polymerase (Promega, WI), and the like.

Incubation of a nucleic acid pool in the presence of a polymerase having a strand-replacement activity may not remove all branch junctions, however. Accordingly, certain embodiments of the present invention are directed to the use of one or more nucleases (during or after amplification) to further reduce branch junctions and/or digest single stranded overhangs in a pool of amplified DNA molecules. In other aspects of the invention, the nuclease enzymatically removes 3' overhangs. Suitable nucleases include, but are not limited to, single-stranded DNA endonucleases such as S1 nuclease.

After removal of hyperbranches, DNA having one or more nicked sequences may remain. Accordingly, in certain embodiments of the present invention, one or more enzymes that repair nicks are utilized (during or after amplification). Suitable enzymes include, but are not limited to, DNA polymerase having a 5' exonuclease activity such as DNA polymerase I, Taq DNA polymerase, any of the modified Taq DNA polymerases, Tfl DNA polymerase (Promega, WI), Tth DNA polymerase (Promega, WI) and the like.

In certain aspects, hyperbranched and/or chimeric sequences are reduced, e.g., in an amplified nucleic acid pool, by at least about 5%, 10%, 15%, 20%, 25%, 30%, 35%, 40%, 45%, 50%, 55%, 60%, 65%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% when compared with nucleic acid pools prior to incubation with an agent that removes hyperbranches and/or an agent that repairs nicks, e.g., a polymerase and/or a nuclease, as described above.

As used herein, the terms "nucleic acid molecule," "nucleic acid sequence," "nucleic acid fragment" and "polynucleotide" are used interchangeably and are intended to include, but not limited to, a polymeric form of nucleotides that may have various lengths, either deoxyribonucleotides or ribonucleotides, or analogs thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, ribozymes, cDNA, recombinant polynucleotides, branched polynucleotides, plasmids, vectors, isolated DNA of a sequence, isolated RNA of a sequence, nucleic acid probes, and primers. Polynucleotides useful in the methods of the invention may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Examples of modified nucleotides include, but are not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, 2,6-diaminopurine and the like. Nucleic acid molecules may also be modified at the base moiety, sugar moiety or phosphate backbone.

As used herein, the term "vector" is intended to include, but is not limited to, a nucleic acid sequence that is capable of transferring an exogenous nucleic acid sequence to target cells. As used herein interchangeably, the terms "vector construct," "expression construct" and "expression vector" are intended to include, but are not limited to, a nucleic acid construct capable of directing the expression of a gene of interest and of transferring that gene to a target cell. Thus, the term includes cloning, and expression vehicles, as well as integration vectors.

Another aspect of the invention pertains to host cells into which a vector of the invention has been introduced. The term "host cell" is understood to refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be a prokaryotic or eukaryotic cell. For example, host cells can be bacterial cells such as $E.\ coli$, insect cells (e.g., $Drosophila$ cells), yeast, or mammalian cells (including, without limitation, Chinese hamster ovary cells (CHO), African green monkey kidney cells (COS), fetal human cells (293T) and stem cells), as well as plant or fungal cells. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including in non-limiting fashion microinjection, calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989, incorporated herein by reference in its entirety for all purposes) and other laboratory manuals.

The following examples are set forth as being representative of the present invention. These examples are not to be construed as limiting the scope of the invention as these and other equivalent embodiments will be apparent in view of the present disclosure, figures, tables, and accompanying claims. The contents of all references, patents and published patent applications cited throughout this application are hereby incorporated by reference in their entirety for all purposes.

EXAMPLE I

Real-Time Ultra-Low Background Isothermal Amplification

The present invention describes a method of polymerase cloning, "ploning," a major technical leap in performing genome analyses at the single-cell level. Ploning provides whole genome amplification from a single DNA sequence with high-yield, high-fidelity, and without significant bias in terms of sequence coverage (Dean et al. (2002) *Proc. Natl. Acad. Sci. U.S.A.* 99:5261; Hosono et al. (2003) *Genome Res.* 13:954; Paez et al. (2004) *Nucleic Acids Res.* 32:e71, each of which is incorporated herein by reference in its entirety for all purposes).

It was hypothesized that the background amplification that currently plagues single-cell MDA arises from two sources: (1) exogenous DNA contamination and (2) endogenous template-independent primer-primer interactions. To assess each source as independently as possible, an ultra-sensitive, sequence-nonspecific detection system was developed (See Example II) to monitor the dynamics of isothermal amplification in real time by SYBR Green I fluorescence (Hafner et al. (2001) *Biotechniques* 30:852, incorporated herein by reference in its entirety for all purposes).

To suppress endogenous background amplification, a constrained-randomized hexanucleotide primer, R6 (R=A/G) which cannot cross-hybridize, was employed. This permitted exogenous DNA contamination present in reagents and lab ware subjected to different preparative procedures to be estimated. Using this readout, a strict sample handling protocol was arrived at (see Example VII) that reliably reduced background amplification to effectively below approximately $10^{-4}$ femtogram/reaction, which is about 10,000 times lower than a single copy of the *E. coli* genome.

Using this ultra-low exogenous background MDA protocol, it was queried whether the level of endogenous background amplification using the totally degenerate primer N6, the most appropriate primer for nonbiased MDA, but most susceptible to primer-primer interactions, was below the femtogram level. Indeed, the effective background of such no-template amplifications were consistently in the approximately 0.03 femtogram range (FIG. 1), opening the door to the ploning of single genomes.

EXAMPLE II

Ultra-Sensitive, Sequence-Nonspecific Detection System

Figure 2:
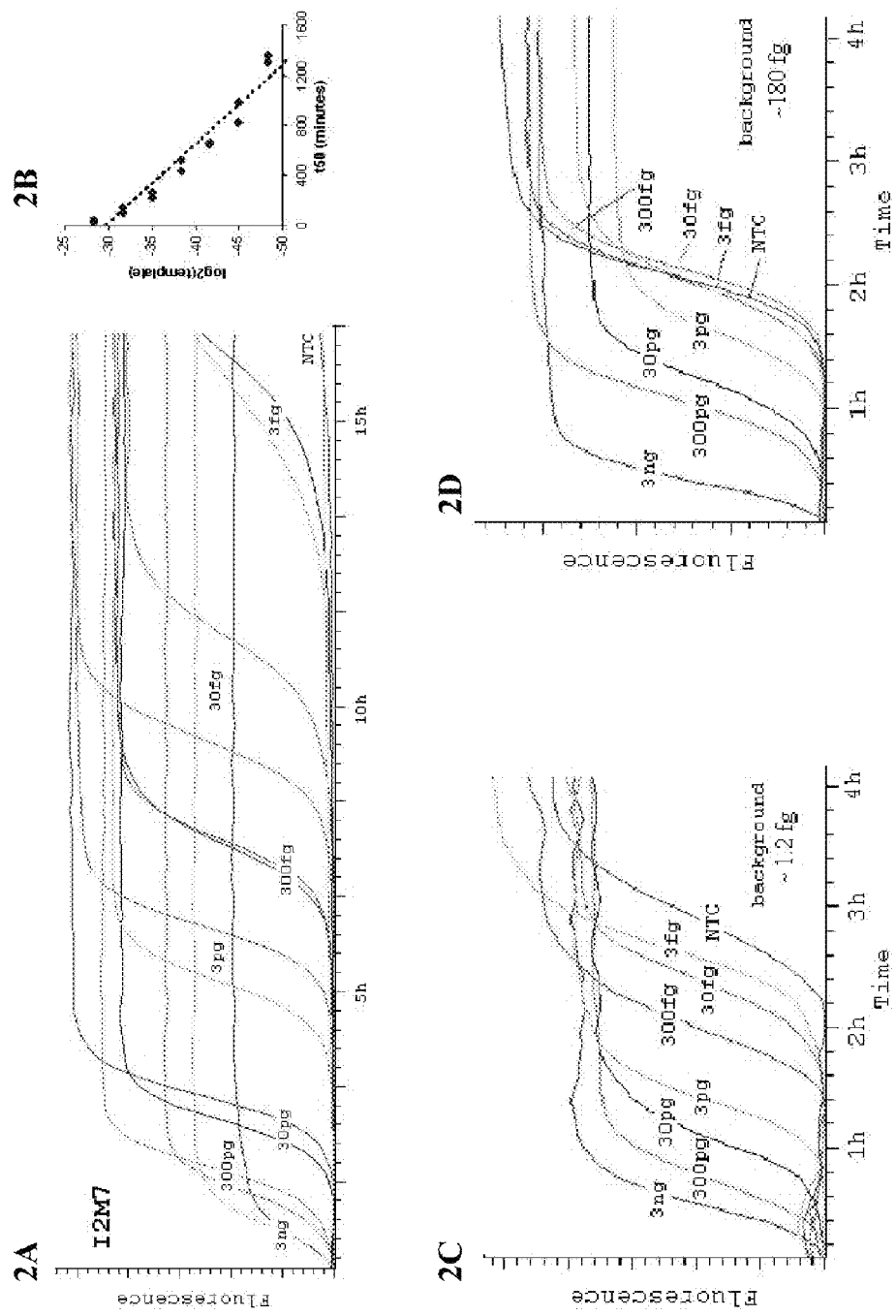
FIGS. 2A-2E depict quantification of amplification background with real-time MDA. (A) Amplification curves for duplicated 10-fold dilution series of human genomic DNA as well as two no-template controls. The time amplification reaches an exponential growth stage was dependent on the amount of template DNA. (B) The time it took an amplification to reach 50% of its saturation level (t50) and the amount of template DNA had a good log-linear fit. (C) When the level of background amplification was low, amplification curves for the 10-fold dilution series were well separated. The doubling time and the level of background contamination could be calculated based on the logistic regression on template amounts and t50 values. (D) The amplification curves at the low end were compressed in the presence of a high level of background, which, without intending to be bound by theory, was probably due to DNA contamination in water. The y-axes are in arbitrary fluorescent units. (E) Amplification background was calculated by projecting the t50 value(s) of the no-template control (NTC) to the best-fit line.
Figure 2:
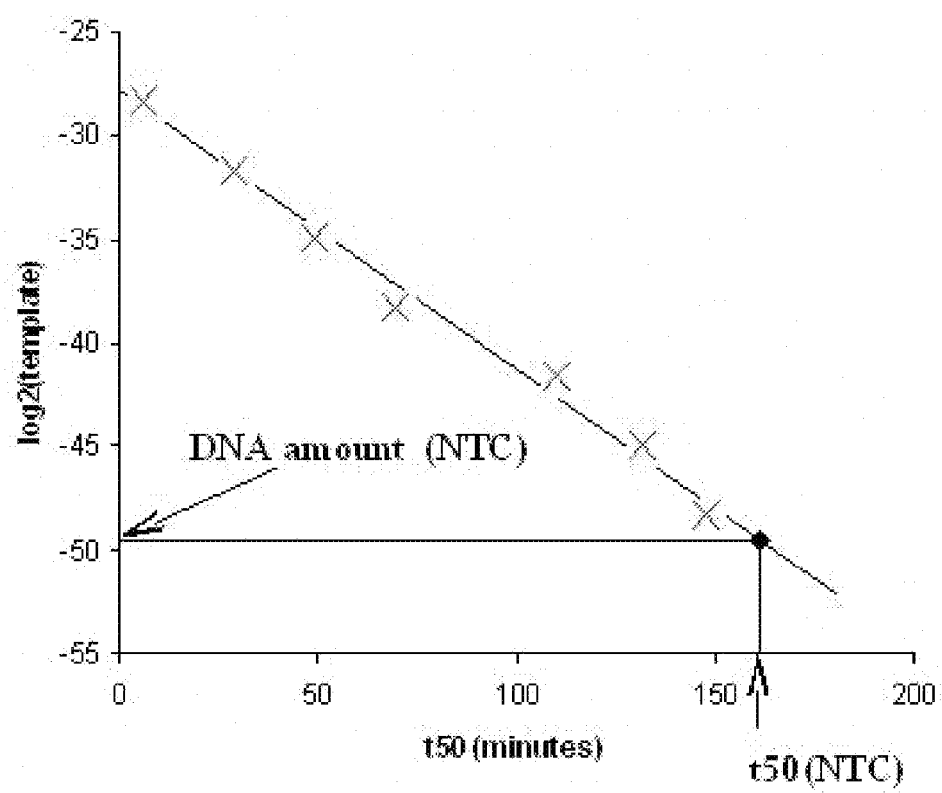
Figure 3:
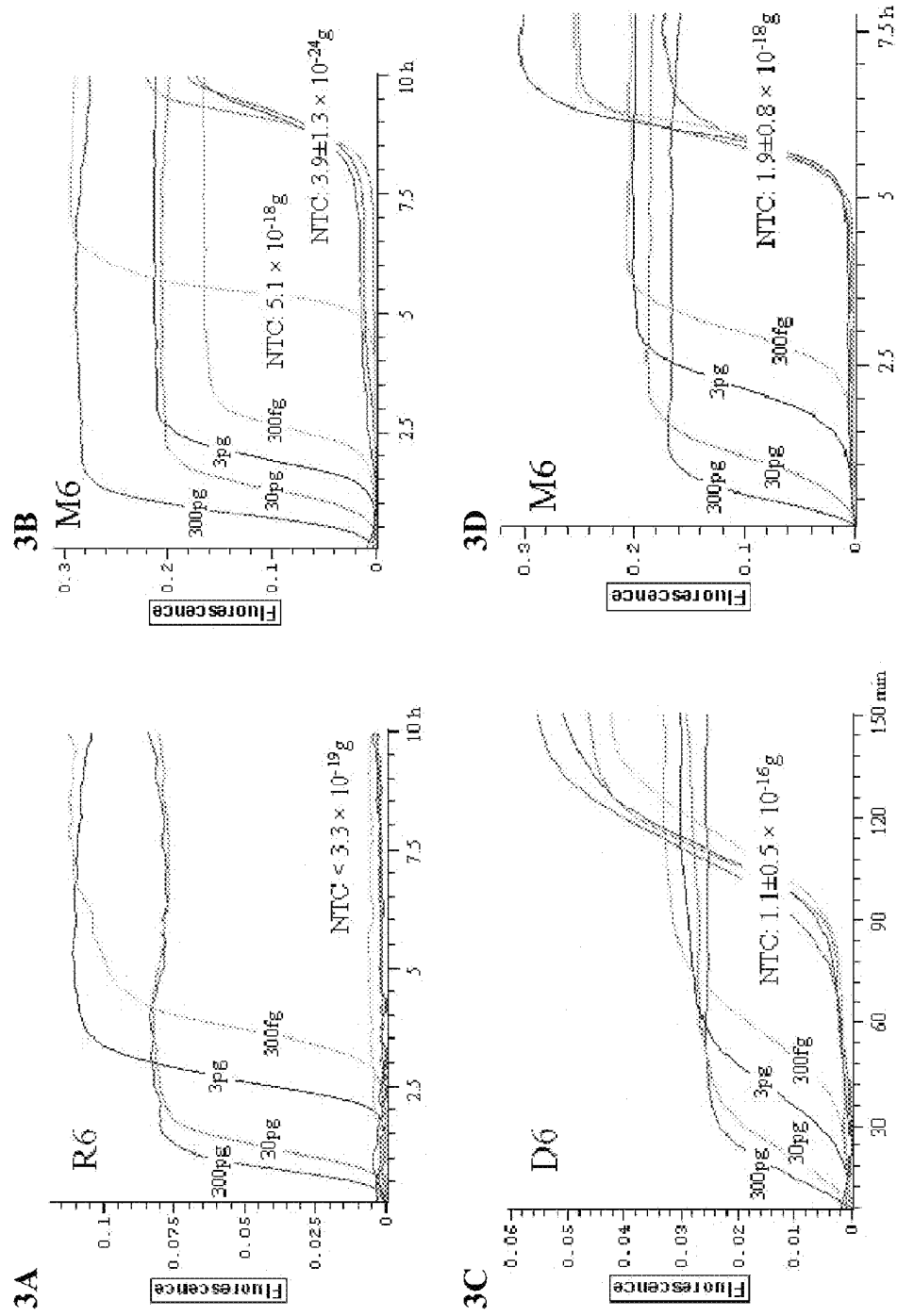
FIGS. 3A-3F depict achieving ultra-low background amplification. (A) The "zero-background" amplification system with the R6 primer. None of the curves for NTC went up, even at the end of the experiment, so the actual background in the system could not be estimated. However, the upper limit of t50 values for the four NTC reactions was ten hours, which is equivalent to a background of $3.3 \times 10^{-19}$ g. (B) Amplifications with the M6 primer also had "ultra-low" background. However, a trace amount of DNA contamination ($5.1 \times 10^{-18}$ g) was present in one no-template control (NTC) reaction, which, without intending to be bound by theory, was likely due to contamination from the reaction tube or cap (i.e., a typical case of random contamination). DNA contaminations in reagents affected all reactions in a consistent manner. Such contaminations were observed in the primer (C), in water (D), or phi29 DNA polymerase (E) (purchased from New England Biolabs). (F) Approximately 1500-fold of background reduction was achieved by UV irradiation on the enzyme (400 mJ/6.4 μl).
Figure 3:
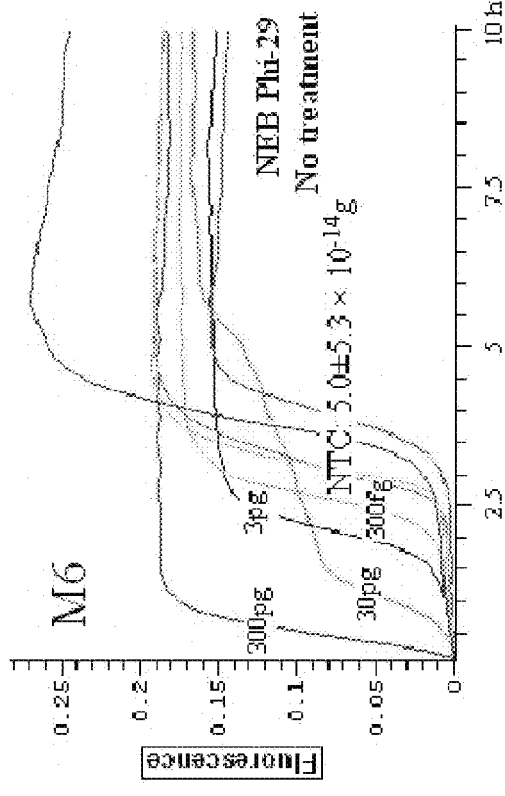

It was determined that MDA, like rolling-circle amplification (Lizardi et al. (1998) *Nat. Genet.* 19:225, incorporated herein by reference in its entirety for all purposes), has an exponential growth stage, and that the time it takes for an amplification to reach its 50% saturation level (t50) is a good summary statistic to capture the underlying amplification dynamics. There is a log-linear relationship between t50 and the amount of DNA templates (FIGS. 2A-B), thus providing a convenient way to estimate background levels. Specifically, the background was calculated by comparing amplification curves from a DNA dilution series with known concentrations. In an amplification system with little background, amplification curves for templates of different concentrations were well separated (FIG. 2C). In contrast, in the presence of background DNA contamination, amplification curves for templates with low concentrations are compressed because template-dependent amplification was masked by background amplification (FIG. 2D). Logistic regression was performed on the t50 values of the well separated curves, and calculated the background based on the best-fit line (FIG. 3). For example, the level of background amplification for the reactions in FIG. 2C was approximately 1.2 femtogram, which is about 150-fold lower than those in FIG. 2D (approximately 180 fg).

To distinguish endogenous background amplification due to primer-primer interaction from exogenous DNA contaminations, a partially degenerate primer, R6 (a random hexameric sequence of A and G), was designed. Because there is no base-pairing potential between any two primer molecules, the amplification system with R6 was expected to have "zero-background" in the absence of exogenous contamination, which was observed experimentally (FIG. 2A). Using the R6 system as reference, common sources of exogenous DNA contamination were identified (FIGS. 2B-E), and a strict sample handling and experimental procedure was developed that reliably reduced endogenous DNA contamination to below approximately $10^{-4}$ femtogram/reaction, which is 10,000 times lower than a single copy of the *E. coli* genome. Using such a protocol, whether N6 and other partially degenerate primers are suitable for single-cell whole genome amplification was investigated. The doubling time, which is defined as the amount of time it takes to generate twice the amount of DNA for amplifications primed by seven degenerate short (6- to 9-mer) oligonucleotides was determined experimentally (Table 1).

Table 1 depicts amplification dynamics and endogenous background of seven primers. To calculate doubling time, amplifications were performed on 10-fold dilution series of human genomic DNA from 3 ng to 3 fg, as well as on no-template controls. Logistic regressions were performed between the template concentrations and the time points that amplification curves reach 50% of their saturated intensities (t50). Pearson R indicated the fit between t50 and the amount of template (log-transformed). The endogenous background was determined with 8U/μl of Epicentre's phi29 DNA polymerase in quadruplicate. All primers had two phosphothioate bonds on the 3' end. N=(A/T/G/C); D=(A/G/T); H=(A/C/T); M=(A/C); R=(A/G); W=(A/C); I=deoxyinosine. "Time Required (hour)*" indicates the amount of time required to achieve $10^8$-fold amplification, calculated based on the doubling time.

TABLE 1

| Primer | Doubling Time (minutes) | Pearson R | Time Required (hour)* | Endogenous Background (g) |
| --- | --- | --- | --- | --- |
| N6 | 5.9 | 0.983 | 2.6 | ~3 × $10^{-17}$ |
| D6 | 7.4 | 0.995 | 3.3 | ~2 × $10^{-23}$ |
| H6 | 18.8 | 0.994 | 8.3 | N.A. |
| M6 | 9.0 | 0.970 | 4.0 | <4 × $10^{-24}$ |
| R6 | 9.7 | 0.955 | 4.3 | <3 × $10^{-19}$ |
| W6 | 10.8 | 0.996 | 4.8 | ~1 × $10^{-22}$ |
| I2M7 | 63.1 | 0.971 | 28.0 | N.A. |

Figure 4:
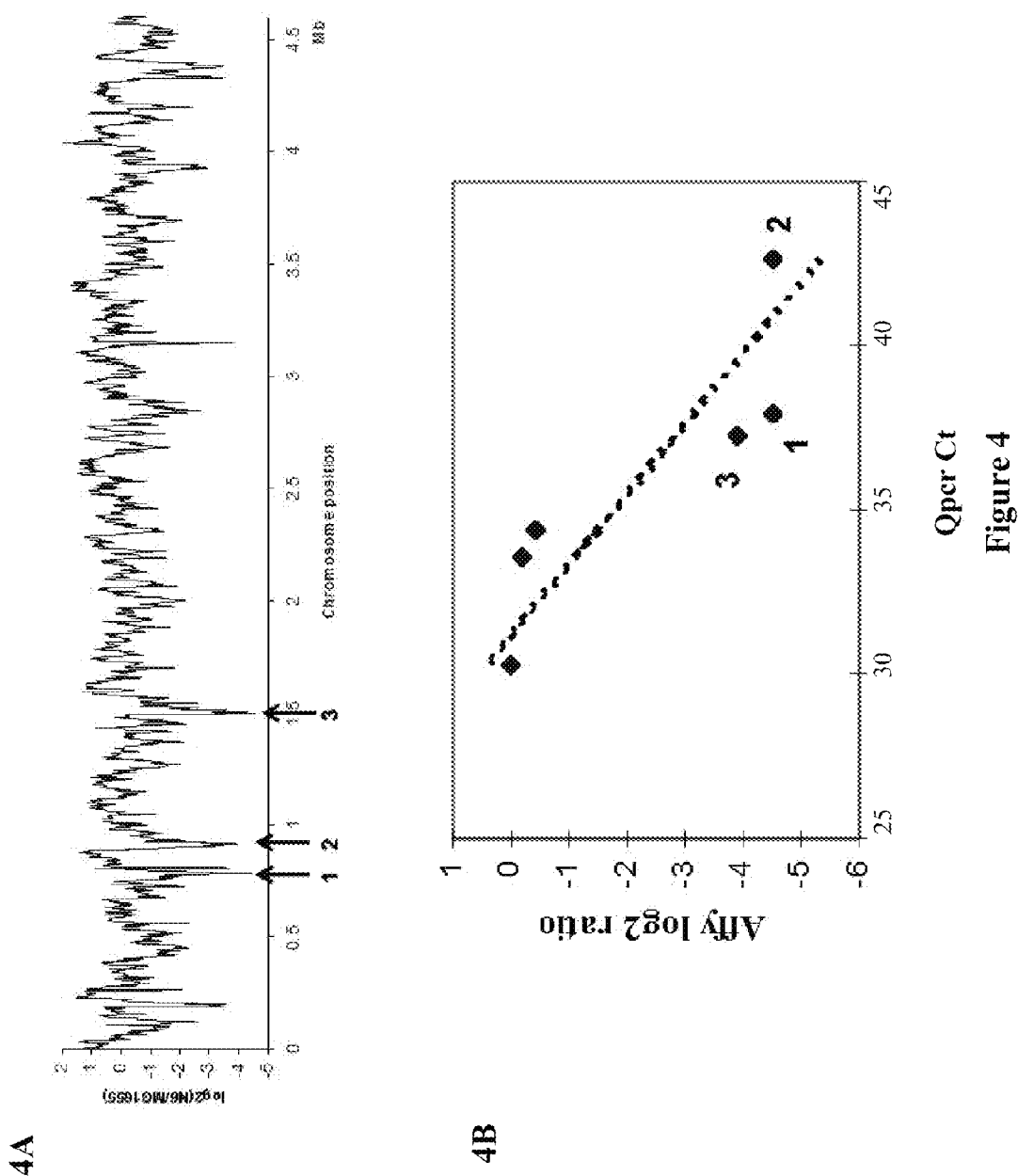
FIG. 4 depicts "dips" of ratio profiles corresponding to genomic regions with low copy numbers. Real-time PCR was performed at six loci, including three corresponding to the three lowest "dips" of the ratio profile (#1, #2 and #3), as well as three other randomly selected loci with hybridization ratios close to the genome average. All the "dips" were successfully recovered by PCR, but clearly represented regions with low copy number.

The endogenous background of these primers was estimated based on the "zero background" amplification system established with the R6 primer. Although the three primers, T2M7, M6 and R6, had no potential for primer-primer interaction, they were excluded as good candidates for whole genome amplification because preliminary analysis revealed that they led to poor genome coverage. For D6, H6 and W6 primers, only A:T base pairs could form, weaker primer-primer interactions was expected to be observed compared with the totally degenerate N6 primer. D6 had a shorter doubling time only second to N6, but an endogenous background amplification that was approximately 100,000 times lower (Table 1). Other factors that affected the amplification dynamics, including primer concentration, enzyme vendor and enzyme concentration, were also investigated (FIG. 4).

Figure 5:
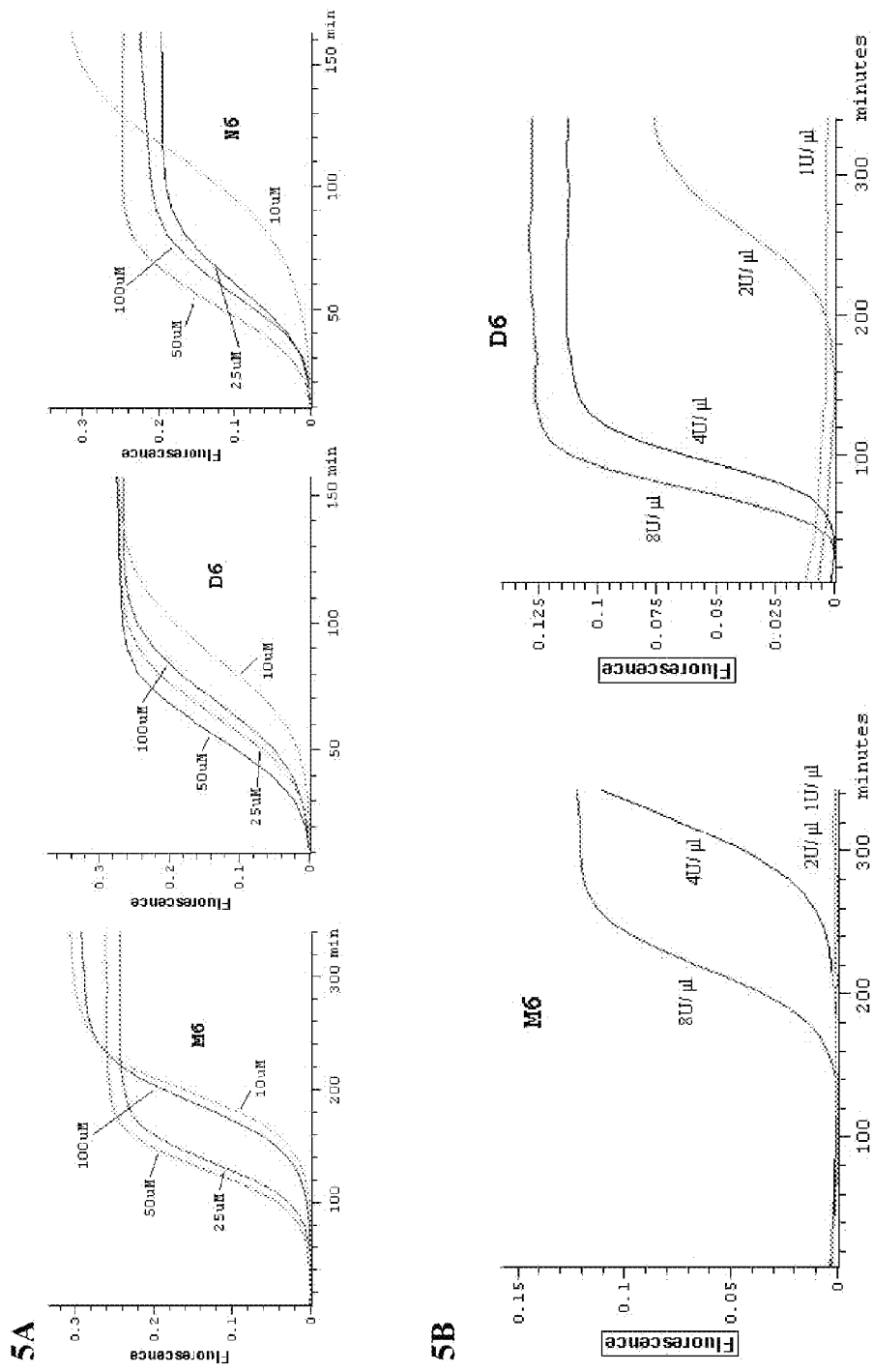
FIGS. 5A-5C depict the effects of (A) primer concentration and (B) enzyme amount on the dynamics of isothermal amplification. The amplification template was 300 pg of human genomic DNA. The y-axes are in arbitrary fluorescent units. (C) Comparison of endogenous background amplification (N=4). The D6 primer had lower endogenous background amplification due to the reduced primer-primer interaction potential. For the N6 primer, a four-fold difference in the concentration of phi29 DNA polymerase lead to an approximately 18,000-fold difference in endogenous background amplification. The y-axis depicts background contamination (g) from 1E-24 to 1E-16.
Figure 5:
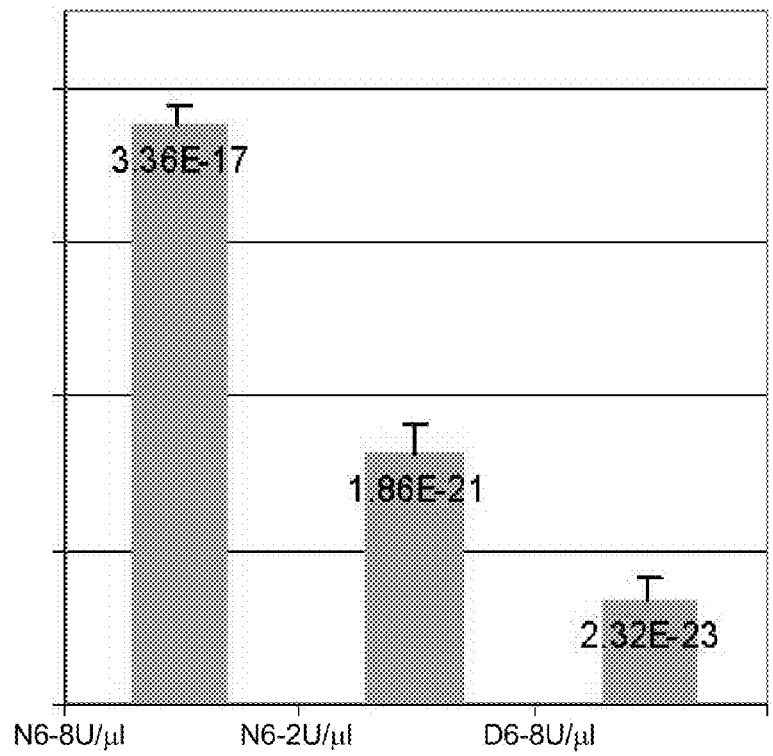

It was determined that, for primers with base-pairing potential, the level of endogenous background amplification depended on the amount of enzyme used. For example, the endogenous background amplification for the N6 primer could be reduced by approximately 18,000 fold using of 2 U/μl instead of the standard concentration 8 U/μl of phi29 DNA polymerase (FIG. 5C). However, even with the standard enzyme concentration used in the original MDA protocol, the endogenous background amplification of N6 was two orders of magnitude lower than the genome mass of a single *E. coli* cell, and thus unlikely to affect amplification coverage. Therefore, to achieve successful amplification from single cell, one should focus on minimizing exogenous DNA contamination instead of endogenous background amplification.

Different levels of background amplification were observed with enzymes from different vendors, and even among different batches from the same vendor. Without intending to be bound by theory, this was likely due to different amounts of DNA contamination in commercial enzymes (Carroll et al. (1999) *J. Clin. Microbiol.* 37:3402; Corless et al. (2000) *J. Clin. Microbiol.* 38:1747, each of which is incorporated herein by reference in its entirety for all purposes). It was determined that an appropriate dosage of UV irradiation could suppress background contamination by approximately 1500-fold (FIGS. 5E-F).

EXAMPLE III

Ploning Single *E. coli* Genomes

Having optimized a protocol to achieve ultra-low exogenous background, an attempt to develop a procedure to plone single cells was pursued. This required a method of assessing whether the obtained amplicon was from truly from a single cell. It was determined that single cells prepared by standard flow-sorting were not suitable for amplification due to the difficulty of preventing contamination introduced during the sorting process. A system was therefore established that utilized a mixture of four *E. coli* strains (NR56, NR57, NR58, NR59, all derivatives of MG1655) that could be genotypically distinguished (see Example IV), and hence allowed verification that the obtained amplicon was indeed clonal. Based on Poisson statistics, when only one strain-specific marker was identified from an appropriate dilution of the mixed cell population, the probability that this amplification was from a single cell was 88%, which is similar to the success rate of flow-sorted single cells (Gray et al (1987) *Science* 238:323, incorporated herein by reference in its entirety for all purposes) (see Example IV for detailed calculation).

Figure 6:
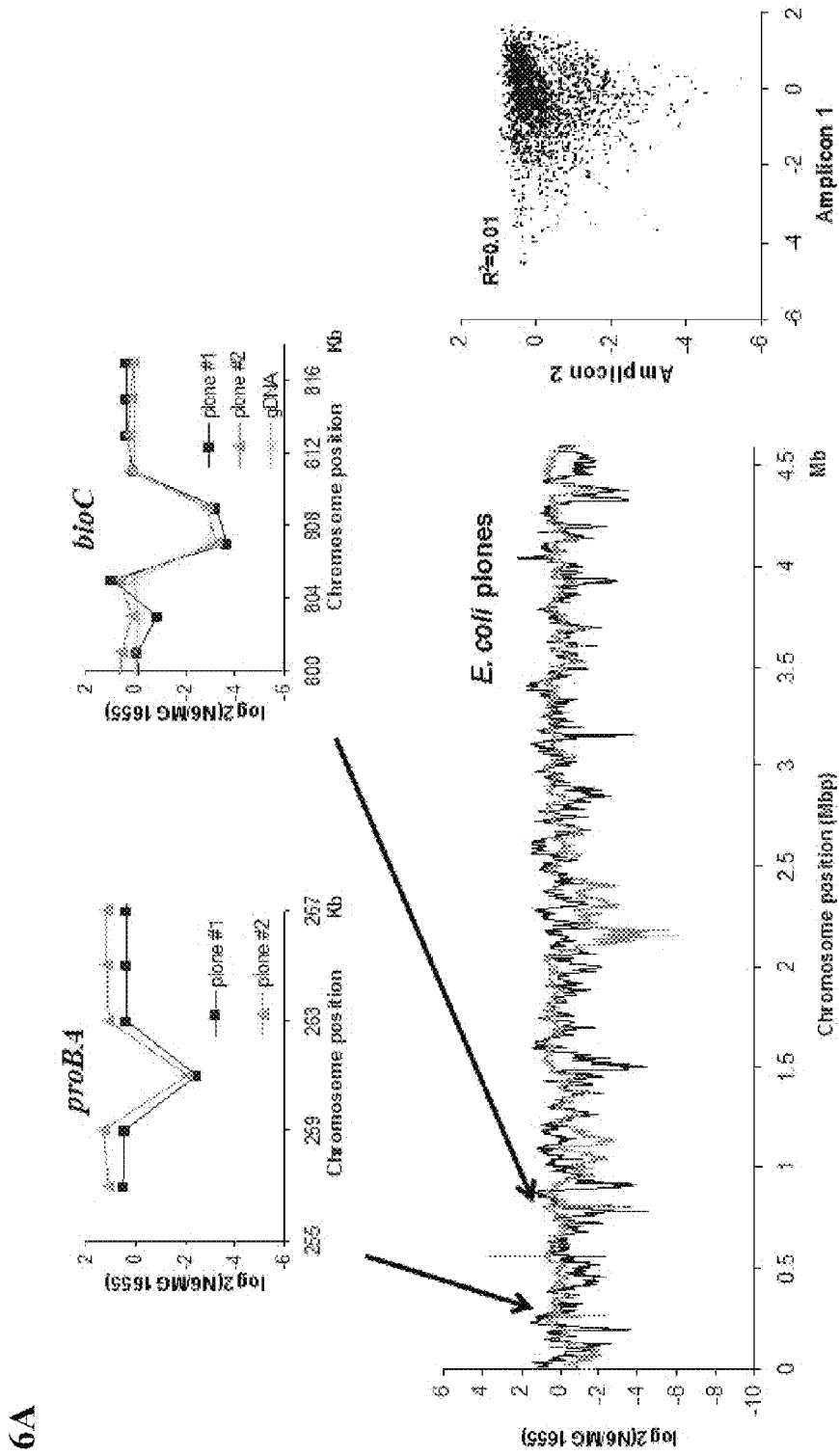
FIGS. 6A-6C depict characterization of plones. (A) Hybridization of two *E. coli* plones to Affymetrix *E. coli* genomic chips showed that the engineered deletions at the bio and proBA (NR57) loci were accurately preserved during amplification. Amplification was not even across the genome. The over- and under-represented regions in two plones do not overlap. In addition, there was little correlation between the ratio profiles of the two plones. (B) The Affymetrix chip hybridization ratios of the *E. coli* plones had wider distribution compared with non-amplified genomic DNA control, indicating that the amplification was biased. (C) Distribution of sequencing depth of plones from two *Prochlorococcus* MIT9312 single cells across genome. The y-axis represents the average number of sequencing reads mapped to a one kilobase window.
Figure 6:
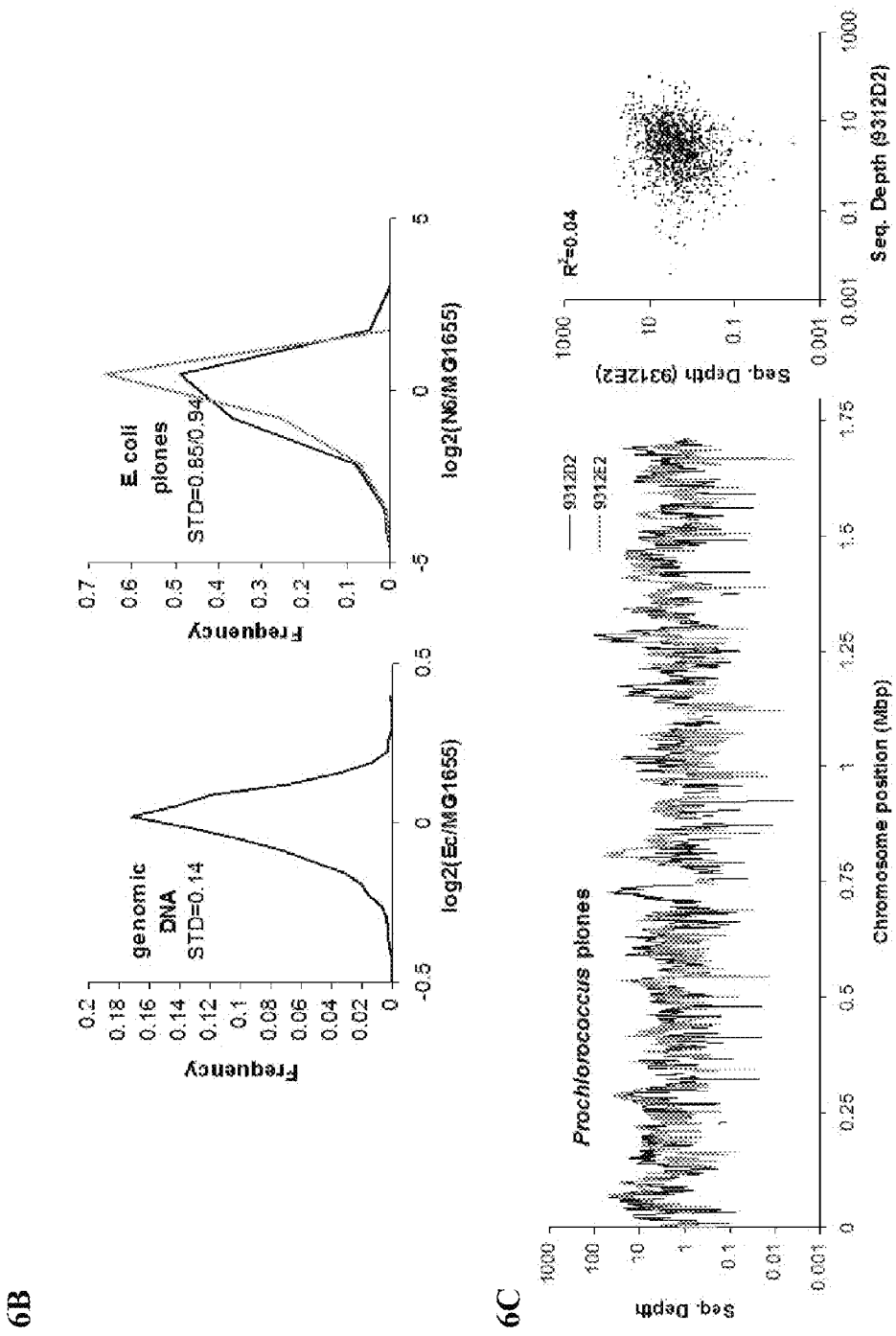
Figure 7:
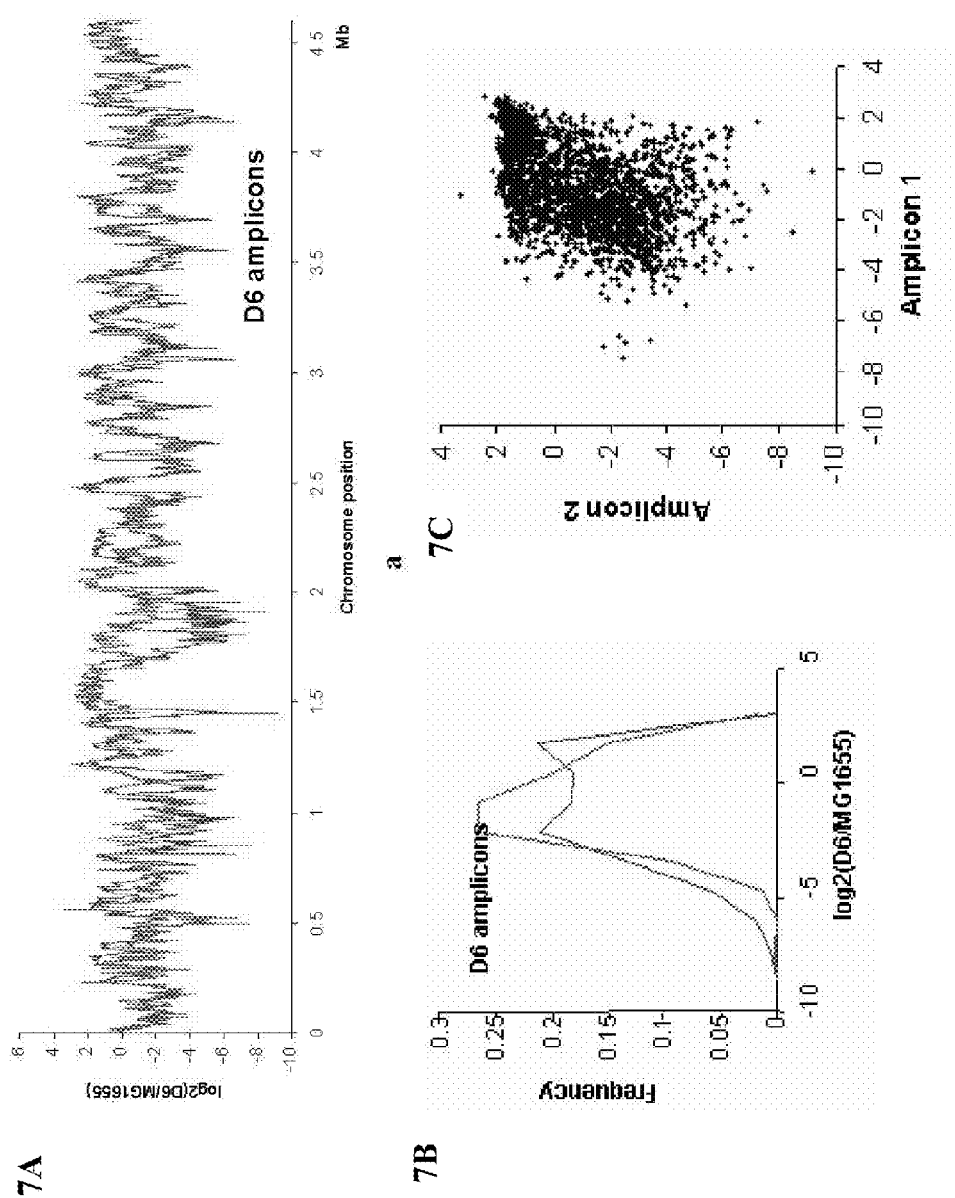
FIGS. 7A-7C depict *E. coli* plones amplified with a restricted-randomized hexamer D6. (A) The ratio profiles the two plones. (B) Variation of the hybridization ratio. (C) Correlation of the hybridization ratios between two plones ($R^2=0.20$).

Ploning reactions were monitored in real-time to ensure a clear kinetic separation of amplification curves of target cells from that of the no-template control (FIG. 1). Two *E. coli* plones were identified, both of which were derived from NR57. Following a second round of amplification to ensure a sufficient quantity of DNA, the specificity, amplification bias and genome coverage were characterized by hybridizing the ploned DNA to Affymetrix *E. coli* Antisense Genome chips. Using *E. coli* MG1655 genomic DNA isolated from cell culture as an unamplified control, the amplified/unamplified ratio of hybridization intensities of 2231 non-overlapping 2 kb windows (covering 96.2% of the *E. coli* genome) was calculated for each plone. This "ratio profile" represented genome-wide relative locus enrichment following amplification (FIG. 6A). Dips in the ratio profile characteristic of the two engineered deletions present in NR57 were detected (FIG. 6A), demonstrating that ploning had a high specificity to the target genome. A 6.5-fold of increase of variability (in $\log_2$ space) was observed in the two plones compared with unamplified reference genomic DNA however (FIG. 6B), indicating various degrees of local over- and under-representation arising from ploning. Without intending to be bound by theory, since a low correlation between ratio profiles of the two independent plones was observed (Pearson $R^2$=0.014), most of the observed ploning bias was likely sequence-nonspecific. To further explore this bias, two *E. coli* plones amplified with the constrained-randomized primer, D6 (D=A/G/T), which is associated with endogenous background orders of magnitude lower than N6, were similarly characterized (Table 1). D6 lead to much higher amplification bias (FIG. 7).

To investigate whether the dips in ratio profiles represented sequences that were completely missing after amplification, real-time quantitative PCR was performed targeting three regions with lowest ratios (FIG. 4). All the three regions were present in the amplicon, albeit in lower copy numbers. Therefore, it was possible recover such underrepresented regions by sequencing at a higher depth or by targeted PCR amplification prior to sequencing.

EXAMPLE IV

Amplification on Single *E. coli* Cells by Limited Dilution of Mixed Cell Population Four strains of *E. coli* (NR56, NR57, NR58, NR59) that were constructed from a common strain EcNR1, a derivative of "wild-type" MG1655 containing a λ Red prophage integrated at the bio locus for use in recombineering were used (Yu et al. (2000) *Proc. Natl. Acad. Sci. U.S.A.* 97:5978, incorporated herein by reference in its entirety for all purposes). Each strain has a particular gene or operon replaced by a chloramphenicol resistance (cat) marker. Accordingly, every strain could be uniquely identified by PCR with strain-specific markers. Like EcNR1, the four strains also shared a common deletion at the bio locus compared with the MG1655 parent, which allowed them to be distinguished from DNA contamination from other laboratory *E. coli* strains. In doing single cell amplification, cells from these four strains were mixed in a 1:1:1:1 ratio and dilutions were made to the single-cell level. Real-time isothermal amplification was then performed followed by PCR on the strain-specific markers. To calculate single-cell probability, the distribution of cell number in one aliquot was assumed to follow a Poisson distribution:

$$P(X=x) = \frac{\lambda^x e^{-\lambda}}{x!}$$

where λ=1, when we made dilutions to the single-cell level. The probability of having 1, 2, 3 or 4 cells in an aliquot was:
P(1-cell)=0.368
P(2-cell)=0.184
P(3-cell)=0.061
P(4-cell)=0.015

For a given amplicon, if only one band was identified by the strain-specific PCR assay, the probability that this amplicon was amplified from a single cell was:

$$P(1-\text{cell} \mid 1-\text{band}) = \frac{P(1-\text{cell})}{\sum_{1}^{\infty} P(1-\text{band} \mid i-\text{cell}) \cdot P(i-\text{cell})}$$

-continued $$\approx \frac{P(1-\text{cell})}{\sum_{1}^{4} P(1-\text{band} \mid i-\text{cell}) \cdot P(i-\text{cell})}$$

And since $$P(1-\text{band} \mid 1-\text{cell}) = 1$$

$$P(1-\text{band} \mid 2-\text{cell}) = 1/4$$

$$P(1-\text{band} \mid 3-\text{cell}) = 1/16$$

$$P(1-\text{band} \mid 4-\text{cell}) = 1/64$$

$$P(1-\text{cell} \mid 1-\text{band}) \approx \frac{0.368}{0.368 + \frac{0.184}{4} + \frac{0.061}{16} + \frac{0.015}{64}}$$

$$= 0.88$$

The 88% success rate was similar to the success rate of flow-sorted single cells (Gray et al. (1987) *Science* 238:323, incorporated herein by reference in its entirety for all purposes). Similarly, when amplifying at the 0.5 cell/reaction level from an equal mixture of three *Prochlorococcus* strains, the success rate was 92% if only one strain-specific marker was detected.

EXAMPLE V

Whole Genome Shotgun Sequencing of *Prochlorococcus* Plones

*Prochlorococcus* (Chisholm (1988) *Nature* 334:340; Partensky et al. (1999) *Microbiol. Mol. Biol. Rev.* 63:106, each of which is incorporated herein by reference in its entirety for all purposes) is one of the most abundant bacterial lineages in the ocean. Although several strains of low- and high-light adapted ecotypes have been identified and sequenced (Rocap et al. (2003) *Nature* 424:1042; Dufresne et al. (2003) *Proc. Natl. Acad. Sci. U.S.A.* 100:10020, each of which is incorporated herein by reference in its entirety for all purposes), *Prochlorococcus* is highly heterogeneous in the open ocean (Urbach and Chisholm (1998) *Limnol. Oceanography* 43:1615, incorporated herein by reference in its entirety for all purposes). The high level of "microheterogeneity" leads to great difficulty in genome assemblies using the environmental shotgun sequencing data (Venter et al, supra; DeLong, supra, each of which is incorporated herein by reference in its entirety for all purposes). Thus, this organism is another model system to conduct proof-of-concept ploning experiments. As described for *E. coli*, cells of three *Prochlorococcus* strains (MIT9312, MIT9313, MED4) were mixed in a 1:1:1 ratio. Cells were stored in 7.5% DMSO at −80° C. to mimic a typical environmental sampling procedure, then ploning was carried out by amplifying at a dilution level of 0.5 cell/reaction. To ensure the presence of single cells in each well, each plone was screened with eighth PCR primer sets specific for each strain. A second round of amplification was performed to generate enough DNA for shotgun library construction and sequencing.

Initial efforts on sequencing such plonal DNA failed due to problems with library construction, including low cloning efficiency, abnormal insert size distribution, and a high percentage of vector sequence among inserts. It was reasoned that these problems arose because of the hyperbranched structure generated during the strand-displacement process of amplification. During library construction, such branched DNA could be ligated into the vector cloning sites, and the branches were resolved by *E. coli* to form chimeras. To resolve the hyperbranched structure, S1 nuclease was used to cleave the junctions of branched DNA molecules, a 3-kb sequencing library was constructed from a MIT9312 *Prochlorococcus* plone (9312E2) using a one-step ligation protocol at the DOE Joint Genome Institute, and shotgun sequencing was performed at 3.5× coverage. 62.2% (including 63.5% of coding sequences and 44.6% intact genes) of the 9312 genome was sampled at least once by 7484 sequencing reads from the 9312E2 library. These raw sequences were assembled into 477 contigs, including 174 that were greater than 2 kb in size. In comparison, in previous efforts of sequencing the MIT9312 strain from a genomic DNA library, the same amount of sequencing reads were assembled into 311 contigs with 211 that were larger than 2 kb.

Although the 9312E2 library represented an improvement upon the initial library, it contained an unusually high percentage of chimeric sequences (19.3%, see Table 2, which depicts the chimeric rates of sequencing libraries from *Prochlorococcus* MIT9312 plones constructed with different post-amplification treatments. Libraries A-C were constructed from the same S1-digested plonal DNA (9312E2) but used three different methods: *Made by JGI with a one-step ligation protocol; +Made by Agencourt with a two-step ligation protocol; Made# with the Invitrogen TOPO cloning system. The Invitrogen TOPO blunt-end cloning protocol was used to make Libraries D-I from the same plonal DNA (9312D2) with different treatments. I and J are two independent libraries generated using the same protocol) and therefore limited the quality of genome assemblies. An improved assembly with longer contigs was obtained when these chimeric sequences were computationally split at their junction points based on the MIT9312 reference genome.

Figure 8:
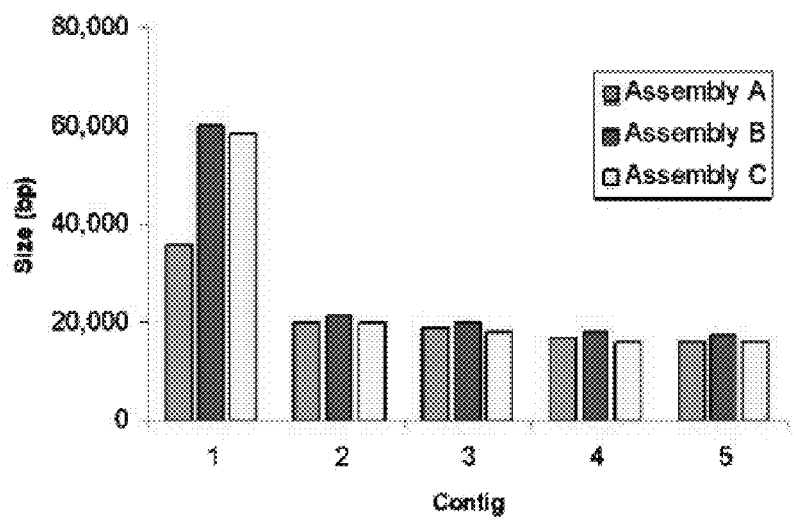
FIGS. 8A-8B depict that breaking chimeric sequences improved genome assembly. (A) The sizes of top five largest contigs in three assemblies of the 9312D2 plone are compared. All raw sequencing reads were used in Assembly A (purple). In Assembly B, chimeric sequences in raw sequencing reads were identified by aligning to the MIT9312 reference genome, and partitioned into fragments at chimeric junctions. Assembly C was obtained at the $5^{th}$ cycle of the iterative assembling procedure, where, without intending to be bound by theory, it is thought that no reference genome is available. (B) The mis-assembly rate of contigs (greater than 5 kb) in three assemblies.
Figure 8:
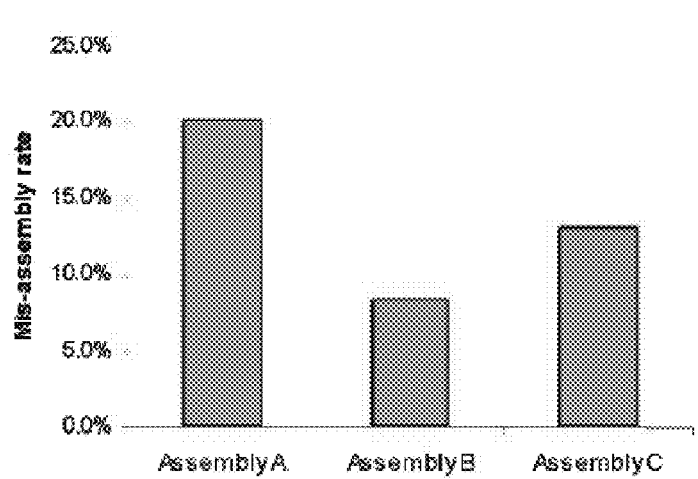

In an effort to improve assembly, advantage was taken of the fact that 85.1% of chimeric junctions could be mapped to genomic regions covered by at least two non-chimeric reads in order to implement an iterative assembly strategy (see Methods). Thus, 698/1481 chimeric reads (47.1%) were able to be identified without the reference genome, generating an assembly of higher quality. The longest contig was improved from 35.4 kb to 58.3 kb, and the percentage of misassembled contigs dropped from 20% to 13% (FIG. 8).

TABLE 2

| Library | phi-29 debranching | S1 Nuclease | Mung Bean Nuclease | T4-Endonuclease VII | DNA Pol I | Chimeric Rate |
|---------|--------------------|-------------|--------------------|--------------------|-----------|---------------|
| A*      | −                  | +           | −                  | −                  | −         | 20.67%        |
| B+      | −                  | +           | −                  | −                  | −         | 18.68%        |
| C#      | −                  | +           | −                  | −                  | −         | 17.00%        |
| D       | −                  | +           | −                  | −                  | +         | 15.63%        |
| E       | +                  | −           | −                  | −                  | +         | 12.50%        |
| F       | +                  | −           | +                  | −                  | +         | 51.28%        |
| G       | −                  | −           | −                  | +                  | +         | 23.40%        |
| H       | −                  | −           | −                  | −                  | +         | 31.82%        |
| I       | +                  | +           | −                  | −                  | +         | 6.25%         |
| J       | +                  | +           | −                  | −                  | +         | 8.33%         |

Figure 9:
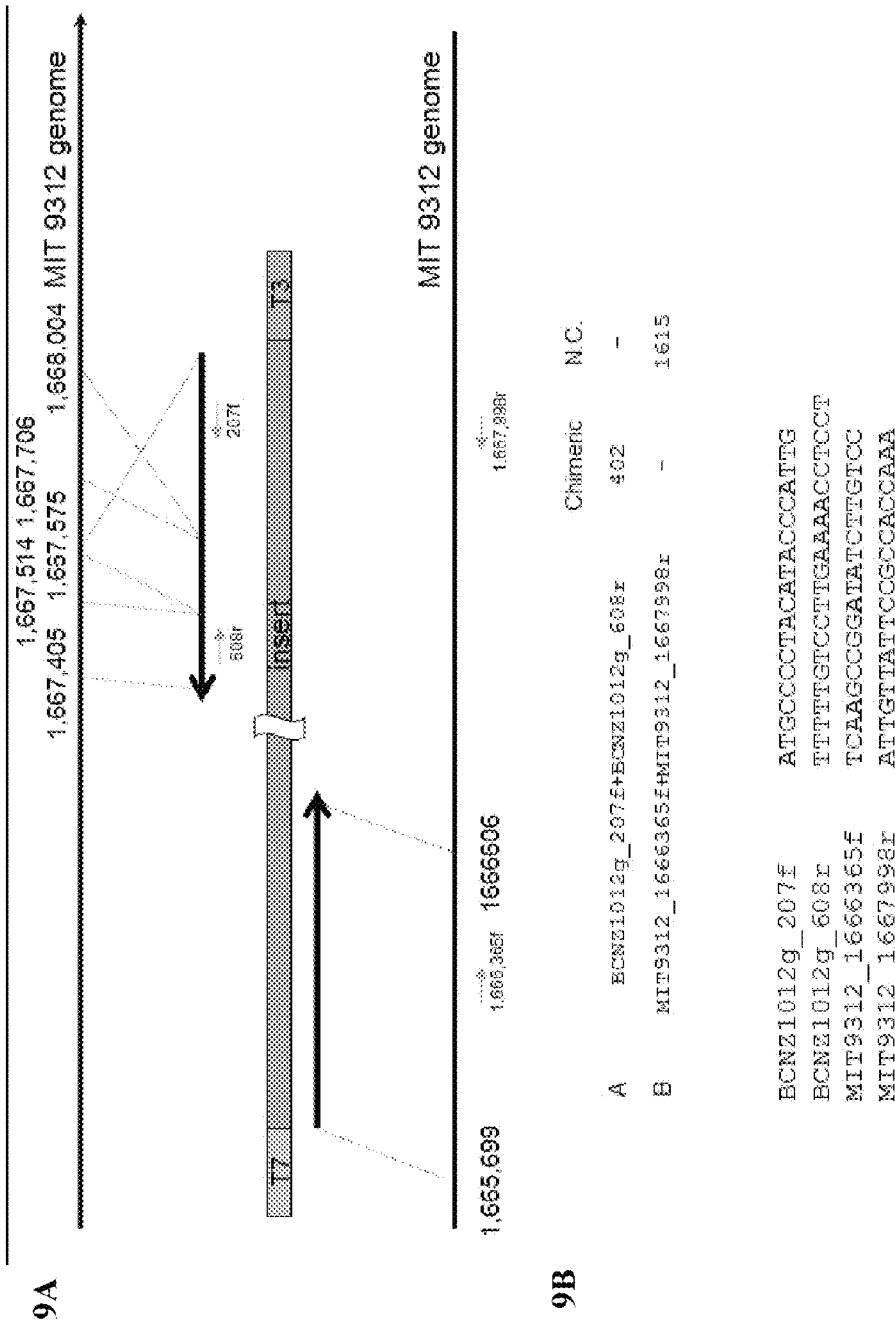
FIGS. 9A-9B depict an investigation of the source of chimera. (A) A typical chimeric clone (BCNZ1012) from a 3-kb shotgun sequencing library constructed by DOE-JGI is shown. The pair-end reads were mapped to the MIT9312 reference genome by Blast, and the chimeric structure was determined. To investigate whether the chimeric sequence existed in the plone prior to library construction, two pairs of PCR primers were designed based on the chimeric sequences and the reference genome respectively, such that when the chimeric sequence existed in the plone, the amplification would be positive with only one primer pair (Amplicon A), and when the plone did not contain the chimeric sequence, the amplification would be positive on another primer pair (Amplicon B). PCR reactions were performed on 20 ng of amplified DNA, which is equivalent to approximately $10^7$ copies of the genome. No chimeric sequences were detected with 30 thermal cycles, indicating that chimera originated post-amplification. The same analysis was performed on four additional chimeric sequences, and no chimeric structures were detected in the plone. The sequence for BCNZ1012g_207F is set forth as SEQ ID NO:3; the sequence for BCNZ1012g_608r is set forth as SEQ ID NO:4; the sequence for MIT9312_1666365f is set forth as SEQ ID NO:5; the sequence for MIT9312_1667998r is set forth as SEQ ID NO:6.

Although almost half of chimeric artifacts could be computationally removed using the iterative assembling procedure described herein, a high chimeric rate could compromise the accuracy of pair-end information and therefore undesirably limit the ploning method to simple genomes. The chimeras seemed to be introduced after ploning, since they were not detected in the plonal DNA by PCR (FIG. 9). Reasoning that the chimeric artifacts were a function of library construction procedure, another library construction procedure was tested using a 2-step oligonucleotide-based ligation procedure. Again, a low cloning efficiency (approximately 20-fold lower than regular genomic DNA) and high chimeric rate (18.7%) were observed. Furthermore, of a total of 5314 pair-end reads obtained from 2657 clones, only 6.5% sequencing reads (465 kb in total length) could be mapped to the reference sequence, the majority of reads being vector sequence. The chimeric rate of a library made by the TOPO cloning method (Invitrogen) was not significantly better (17%, see Table 2).

Figure 10:
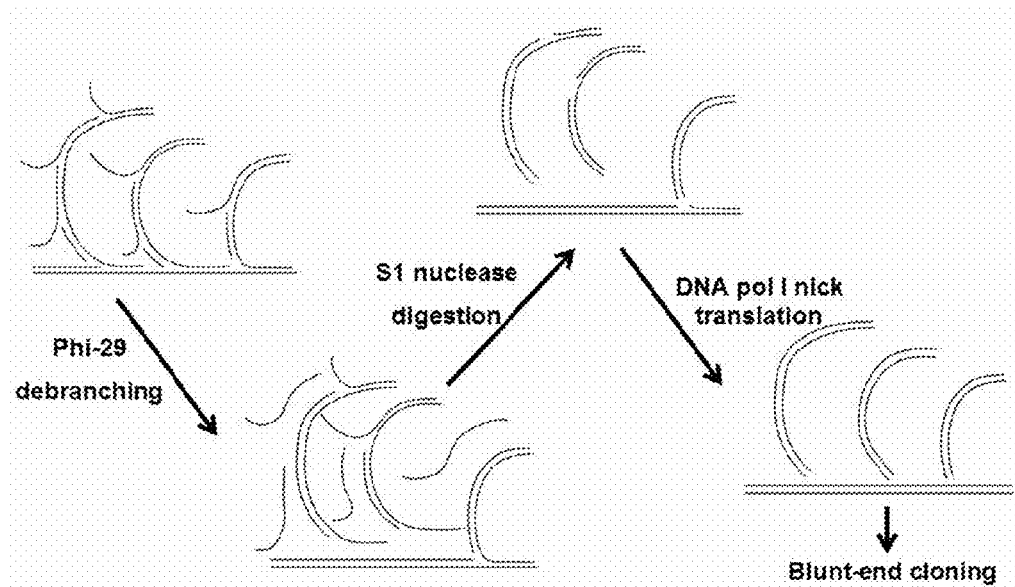
FIG. 10 depicts a schematic of a method for resolving hyperbranched DNA structure for sequencing library construction. In the first step, hyperbranched DNA was incubated with phi29 DNA polymerase and dNTPs, but without any primer. Because of the strand-replacement activity of the phi29 polymerase, the density of branching junctions was reduced. This step also gave rise to some 3' single-stranded overhangs. Junctions were broken by S1 nuclease digestion at the second step. 3' single-stranded overhangs were also removed. The resulting DNA molecules were double-stranded with some nicks. After shearing and gel-size selection, these nicks were removed by nick translation using DNA polymerase I, which has not only polymerase activity, but also 5'- and 3'-exonuclease activities.

It was hypothesized that even after S1 nuclease treatment, plonal DNA retained enough non-canonical structure to interfere with cloning. To address this, other post-amplification enzymatic treatments were tested (Table 2). Different chimeric rates were observed with different treatments on the same plonal DNA, confirming that chimeras were generated during library construction. A chimeric rate as low as 6.25% was achieved with the combination of three treatments: phi 29 polymerase de-branching, S1 nuclease digestion, and DNA polymerase I nick translation. Skipping any of these treatments resulted in higher chimeric rates, indicating a three-step model of linearizing hyperbranched DNA (FIG. 10).

Figure 11:
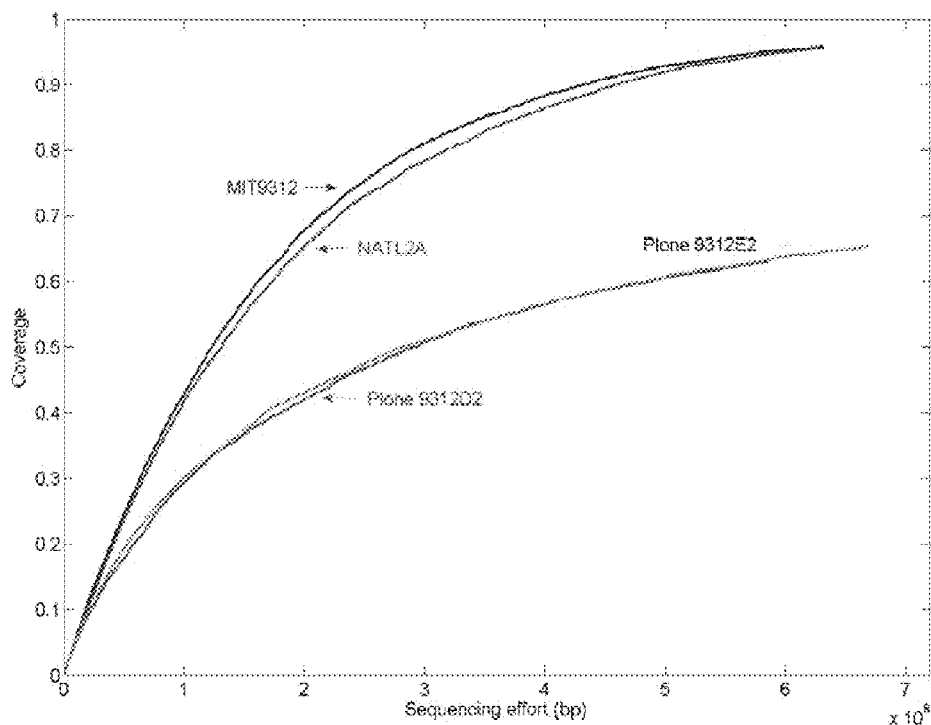
FIG. 11 depicts genome coverage as function of genome sequencing effort of genomic DNA from two *Prochlorococcus* strains (MIT9312, size 1.71 Mbp, (blue) and NATL2A, size 1.84 Mbp (green)) and DNA from two MIT9312 plones (red and turquoise).
Figure 12:
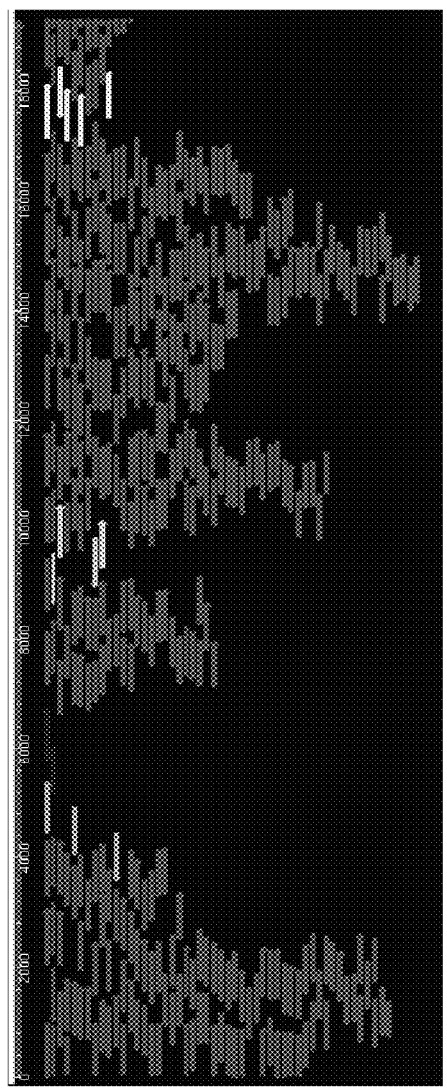
FIGS. 12A-12B depicts uneven read depth due to amplification bias. (A) Phrapview of raw sequencing reads from the 9312E2 plone aligned to a contig. Regions of high read depth (greater than 10×) alternated with regions with very low read depth (approximately 1× to 2×). (B) Phrapview of sequencing reads from the ACCW library (constructed from MIT9312 unamplified DNA). Read depth was more even across the contig. The x-axis represents position on the contigs.
Figure 12:
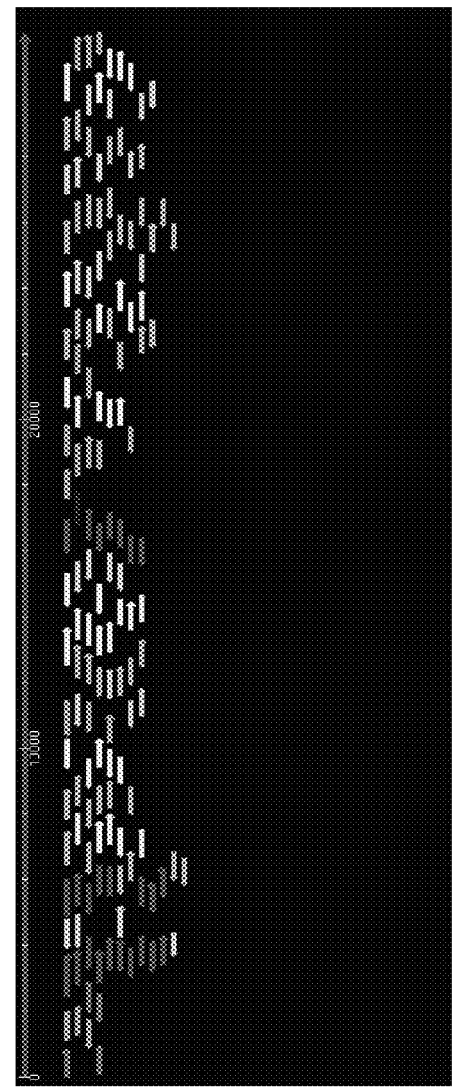
Figure 13:
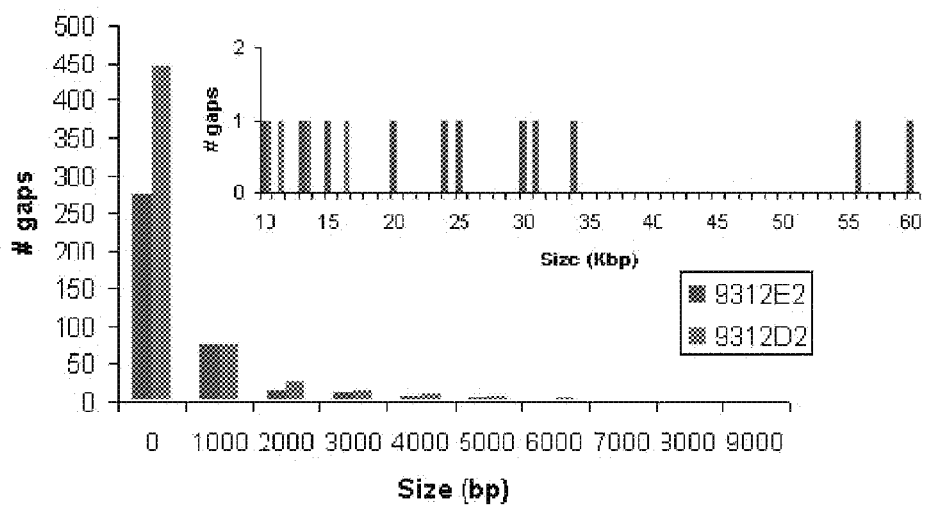
FIG. 13 depicts size distribution of the unsampled regions in the two *Prochlorococcus* plones. Sequences were recovered within gaps with PCR. Amplicons A and B (chromosome location: 1110857-1112538, 1112508-1114078) were located in the biggest gap in the 9312D2 plone. Amplicons C and D (chromosome location: 698815700414, 700362-701934) were located in the biggest gap in the 9312E2 plone. Unamplified MIT9312 genomic DNA was used as a positive control.

A sequencing library for a second plone (9312D2) was constructed using the new library construction protocol, and was sequenced to a depth of 4.7×. Approximately 66.0% of the genome was recovered with a total of 7.2 Mb of high quality reads (largest gap was 17 kb). Because of the biases introduced by amplification, ploning requires more total sequencing to achieve the same level of coverage as that obtained from unamplified genomic DNA (FIG. 11). At a comparable level of sequencing depth, approximately 96.4% of the genome could be recovered from unamplified MIT9312 genomic DNA. Due to the biases inherent to single molecule amplification, some genomic regions were repeatedly sampled while others are barely covered once (FIG. 6C, FIG. 12). By fitting the coverage curves in FIG. 11, it was estimated that it would take approximately 26 Mbp (approximately 15×) of sequencing reads to sample 90% of the *Prochlorococcus* genome. Alternatively, the unsampled regions could be amplified by PCR on the plones and sequenced. To illustrate the feasibility of this approach, primers were designed to target the center regions of the largest gaps in the two *Prochlorococcus* plones. All the target regions were successfully recovered (FIG. 13), which was consistent with the real-time PCR results with the *E. coli* plones.

10 sequencing reads (0.09%) were observed in the 9312D2 library and 12 (0.16%) were observed in the 9312E2 library that did not share homology with any known sequences in the NCBI nr database. Without intending to be bound by theory, these were likely artificial sequences generated by N6 primer-primer interaction (endogenous background amplification). There were also two sequencing reads (0.02%) in the 9312D2 library and 74 (1%) in the 9312E2 library that mapped to the MED4 genome. Without intending to be bound by theory, these sequences were likely amplified from DNA from lysed MED4 cells in the initial mixture cell population. No other known sequence (except for the target genome, MIT9312) was detected in the libraries, confirming that the ploning method had extremely low background.

To identify potential mutations that could have arisen during single cell amplification, the largest contig of the 9312E2 plone (59,652 bp) was compared with the reference genome, and 81 mismatches were identified. Visual inspection was performed at the assembly at each of the mismatched positions, and it was determined that all of the mismatches were due to assembly errors or discrepancies among raw reads, especially in homopolymeric regions (i.e., some reads had five Ts in a row and others had four). Not a single mismatch was observed that was not due to a sequencing error. Therefore, the estimated amplification error was less than $1.7\times10^{-5}$, well below the Bermuda standard for genome sequencing ($10^{-4}$).

EXAMPLE VI

Ploning of "Wild" *Prochlorococcus* Cells

Figure 14:
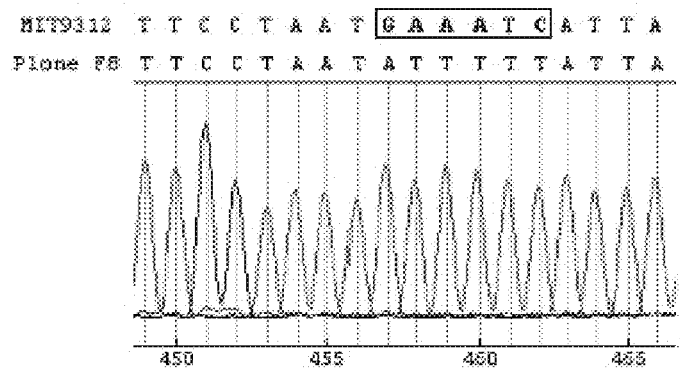
FIGS. 14A-14B depict the characterization of two *Prochlorococcus* plones from an ocean sample. (A) Natural variation in part of the ITS sequence compared with the MIT9312 lab strain. The MIT9312 sequence is set forth as SEQ ID NO:7; the Plone F8 sequence is set forth as SEQ ID NO:8. (B) Mapping positions of the trial sequencing reads from the two HOT plones. The same number of sequencing reads were randomly sampled from the 9312D2 and 9312E2 shotgun sequencing libraries for comparison.
Figure 14:
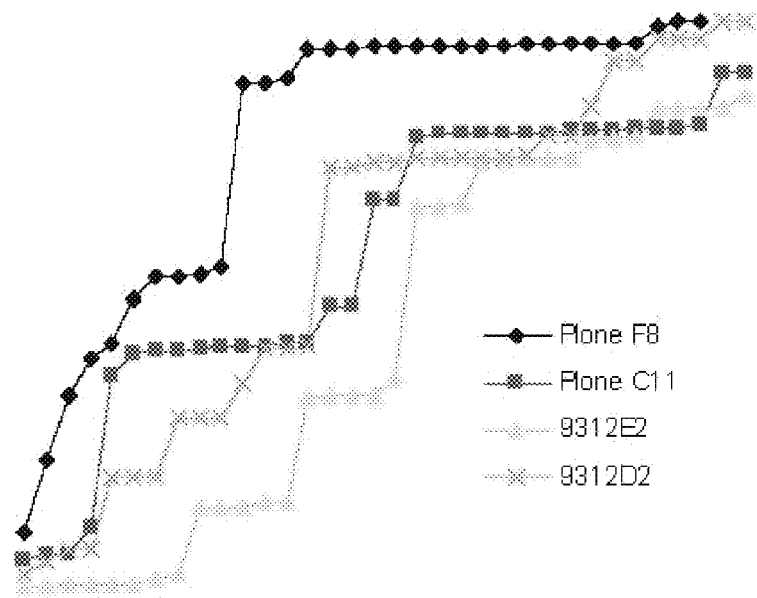

Having established the ploning method using lab strains of *E. coli* K-12 and *Prochlorococcus* MIT9312, this method was next applied to a Pacific Ocean sample collected at the depth of 85m in October 2003 at the Station ALOHA (2'45'N, 158'00'W) under the Hawaii Ocean Time-series project. Two single *Prochlorococcus* cells were successfully ploned. Sequencing of the 16S rDNA and the *Prochlorococcus* specific ITS (Internal Transcribed Spacers of the ribosomal operon) indicated that both cells are closely related to the MIT9312 strain. Trial sequencing was performed of two shotgun libraries, and a similar level of bias in genome coverage was observed as detected in the 9312D2 and 9312E2 plones (FIG. 14). The average sequence identity to the MIT9312 genome was 91.7% for both plones, and these two plones also differed between themselves. Full genome shotgun sequencing of these two plones is currently being undertaken and will elucidate the level of genome diversity between lab strains and cells in the wild.

EXAMPLE VII

Materials and Methods

Ultra-Low Background Real-Time Isothermal Amplification

A strict sample handling and experimental procedure was developed and determined to be essential to achieve sub-femtogram levels of background. All experiments were conducted in an AirClean 1000 PCR hood (AirClean System, NC) with a dedicated set of pipettes. Unopened pipette tips were used for every experiment. Tubes, tube caps and all reagents, except for the primers, dNTPs, SYBR Green I and polymerases, were treated with UV for approximately five to ten minutes in a Stratalinker (Stratagene, CA, model # 1800). Primers and SYBR Green I were diluted with UV-treated RT-PCR grade water (Ambion, TX). Isothermal amplifications that contained various amount of templates, 8U/μl RepliPHI phi29 DNA polymerase (Epicentre, WI), 1 mM dNTP, 1 mM N6 primer with two 3' phosphothioate bonds (Dean et al. (2001) *Genome Res.* 11:1095, incorporated herein by reference in its entirety for all purposes), 0.1× SYBR Green I (Molecular Probes, OR) and 1× RepliPHI reaction buffer were performed in 20 μl or 50 μl volume in a real-time PCR thermocycler (Opticon 2, MJ Research, MA) at 30° C. for ten hours. Fluorescent intensities were collected via the SYBR Green I channel every six or fifteen minutes. Random primers were purchased from IDT (IL). When necessary, the phi29 DNA polymerase was UV-treated in inverted strip-tube caps placed on top of a chilled 96-well PCR cooler (Eppendorf, Germany) filled with water to avoid sample heating. Real-time isothermal amplification data were exported by the Opticon2 program, and analyzed using a Perl script.

Polymerase Cloning on E. coli and Prochlorococcus

Six E. coli strains, MG1655, EcNR1, NR56, NR57, NR58 and NR59 were cultured in LB medium in a 30° C. shaker overnight. NR1 is MG1655 with a defective λ phage in place of the bioA and bioF genes and was used to construct the four strains by recombineering (Yu et al. (2000) Proc. Natl. Acad. Sci. U.S.A. 97:5978, incorporated herein by reference in its entirety for all purposes). Each of these strains has a cat marker replacing a particular gene operon, i.e., NR56 is NR1 ΔglyA::cat, NR57 is NR1 ΔproBA::cat, NR58 is NR1 Δthr-BC::cat, and NR59 is NR1 ΔtrpLEDBCA::cat. Genomic DNA from the MG1655 strain and EcNR1 strain were extracted with the QIAGEN Genomic-tip 20/G (Qiagen, CA). To prepare single-cell dilutions, cells of strains NR56, NR57, NR58 and NR59 were washed twice in UV-treated PBS. Cell densities were determined by direct counting using a hemacytometer. Cells were then mixed in equal ratios, and diluted to the single-cell level. Cell density was re-confirmed by performing 364-plex, single-cell, PCR reactions on single cell dilutions using the strain specific primers, and checking PCR products by electrophoresis.

Single-cell dilutions were treated with ten units of lysozyme at room temperature for ten minutes prior to amplification, and denatured by alkaline solution as described in Dean et al. (Dean et al., supra, incorporated herein by reference in its entirety for all purposes). After real-time isothermal amplification at 30° C. for ten hours, single-plex PCR was performed with the same primer set on the amplicons in order to identify those that were amplified from single cells. The HotStar PCR MasterMix (Qiagen, CA) for PCR amplification was used with one µl of 1:100 diluted amplicons (or one µl of single cell dilution) and a final primer concentration of 0.2 µM. The thermocycling protocol was: 95° C. for 15 minutes followed by 35 cycles of 94° C. for 30 seconds, 64° C. for 30 seconds, and 72° C. for 30 seconds, and a final step of 3 minutes at 72° C. PCR products were checked by gel electrophoresis. In order to prepare sufficient DNA from single-cell amplicons for both Affymetrix chip hybridizations and library construction, a second round of amplification was performed on the amplicons using the standard MDA protocol. Id. Real-time quantitative PCR assays confirmed that additional locus-specific biases introduced in this step was negligible compared with the first round amplification.

To prepare Prochlorococcus plones, cells of three lab strains (MIT9312, MIT9313, MED4) were mixed in 1:1:1 ratio and stored in 7.5% DMSO at −80° C. Cell density was determined with flow cytometry. Amplification was performed at the dilution level of 0.5 cell/aliquot. Amplicons were 1:100 diluted and screened for positive Prochlorococcus plones by performing PCR with primers targeting the Internal Transcribed Spacers of the ribosomal operon (ITS, 2F: GAAGTCGTTACTCCAACCC (SEQ ID NO:1); 3R: TCATCGCCTCTGTGT GCC (SEQ ID NO:2)).

Affymetrix E. coli Chip Hybridization and Analysis

Single cell amplicons were purified with Microcon YM30 columns (Millipore, MA), and fragmentation was performed with DNase I (Amersham, NJ). Labeling was performed with the BioArray terminal labeling kit (Affymetrix, CA). Unamplified genomic DNAs from EcNR1 and MG1655 were hybridized in triplicate and very low inter-experiment variation was observed. Therefore, one hybridization experiment was performed for each of the four amplicons. Hybridization and scanning were performed using approximately 2 µg of labeled DNA by the Biopolymer Core Facility (Harvard Medical School). Data analyses were primarily conducted using the Bioconductor Affymetrix package (Worldwide Web site: "bioconductor.org", incorporated herein by reference in its entirety for all purposes) with a customized probe set package, in which probes were grouped into non-overlapping two kb bins along the chromosome.

To reduce potential cross-hybridization signals, BLAST searches were performed for all probes on the Affymetrix E. coli Antisense Genome chip against the E. coli $K_{12}$ genome sequence (GenBank ACC: NC_000913), and those having more than one match of greater than 75% identity were excluded. As a result, the analyses were based on a total of 133,203 pairs of PMMM probes. The oligonucleotide probes on the Affymetrix chip were not evenly spaced across the genome, so that the two kb bins did not have an equal number of probes. Because too few probes may lead to probe-specific bias, bins having less than ten probes were excluded. Additional probe sets (each containing ten pairs of probes) representing the four strain-specific deletion regions were included because a bin size of two kb was too large compared with the size of these deletions.

The average normalized intensity of the three MG1655 replicates at each two kb bin was used (as denominators) to calculate the ratios for the other experiment in order to cancel the hybridization biases at the probe set level. The Bioconductor Affymetrix package provided several different methods for background correction, normalization and probe set summary. The performance of all methods were compared based on the results at the bio locus, and it was determined that the MAS5 method was most appropriate for the study presented herein. Accordingly, all analyses were based on the results generated by MAS5.

Shotgun Sequencing Library Construction

To prepare a sufficient amount of DNA from the 9312D2 plone for library construction, a second round of amplification was performed on greater than one µg of plone DNA using the regular MDA protocol. The amplicon was purified using a Microcon YM-100 column, then incubated with 8 U/µl RepliPHI phi29 DNA polymerase, 1 mM dNTP and 1× RepliPHI reaction buffer in 50 µl at 30° C. for two hours, at 65° C. for three minutes, and then digested with 1 U/µl S1 nuclease (USB) in 200 µl 1× buffer (30 mM NaAc, pH 4.5, 50 mM NaCl, 1 mM $ZnCl_2$) at 37° C. for 30 minutes. Debranched DNA was extracted with phenol/chloroform, and sheared using a homemade shearing device (equivalent to Genomic Solutions' HydroShear) at speed code 13. Sheared DNA was concentrated with Microcon YM-100 column (Millipore), size selected by agarose gel electrophoresis, and purified using Qiaquick gel extraction kit (Qiagen). DNA (100 ng to 1 µg) was polished with 3U of T4 DNA polymerase (New England Biolabs) and 10 U of DNA polymerase I (Invitrogen) in 50 µl of 1×NEB buffer 2 and 0.5 mM dNTP at room temperature for one hour, inactivated at 75° C. for ten minutes, and dephosphorylated by adding 50 U of calf intestinal phosphatase (New England Biolabs), 10 µl of NEB buffer 3 (10×) and 35 µl $dH_2O$ and incubating at 37° C. for one hour.

After extraction with phenol/chloroform and purification with ethanol precipitation, four µl of DNA (approximately 30 to 100 ng) was incubated with 1 µl pCR4Blunt TOPO vector (Invitrogen) and 1 µl salt solution (Invitrogen) at room temperature for 15 minutes. Ligation product was purified by ethanol precipitation, resuspended in three µl $dH_2O$, and transfected into 50 µl of TOP10 ElectroComp cells (Invitrogen) by electroporation at 20 kV. The transformation reaction was incubated in 500 µl SOC media in a 37° C. shaker at 250-rpm for one hour, and stored at −80° C. with 20% glycerol before plating.

Whole genome shotgun sequencing of the 9312D2 plone was conducted at Agencourt Biosciences using oligo-based adaptor ligation for library construction. For the 9312E2 plone, DNA was only digested with S1 nuclease after amplification, and the library was constructed and sequenced at DOE Joint Genome Institute (JGI) with JGI's standard prtoool (at the Worldwide Web site: "jgi.doe.gov/sequencing/protocols/prots_production.html", incorporated herein by reference in its entirety for all purposes). Small-scale sequencing was conducted at the HMS Biopolymers Facility or Genaissance Pharmaceuticals (CT). Sequence analyses/genome assembling was performed in-house using phred/phrap/consed or at the DOE Joint Genome Institute.

Iterative Genome Assembling

To improve genome assembly in the presence of chimeric sequences, multiple rounds of genome assembling and chimeric sequence detection were performed: (i) all reads were assembled into contigs using Phrap; (ii) all contigs were assumed to be non-chimeric, and all raw reads were compared with the contigs, chimeric sequences were detected and they were broken at each chimeric junction; (iii) the resulting sequences were fed into to Phrap for the next round of assembly. This iterative assembling procedure was repeated until the chimeric rate stopped improving. This algorithm was implemented with Perl and available at the Worldwide Web site: "arep.med.harvard.edu/kzhang/Ploning/Iterative Assembler.zip", incorporated herein by reference in its entirety for all purposes.

EXAMPLE VIII

References

Each of the following references is incorporated herein by reference in its entirety for all purposes.

Panelli et al. (2005) *Biotechniques* 39:174
Shendure et al. (2005) *Science* 309:1728
Margulies et al. (2005) *Nature* 437:376
Thompson et al. (2005) *Science* 307:1311
Acinas et al. (2004) *Nature* 430:551

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention.

---

What is claimed is:

1. A method of amplifying a nucleic acid sequence from a single cell comprising:
   amplifying a nucleic acid sequence from a single cell to produce an amplified nucleic acid sequence; and
   contacting said amplified nucleic acid sequence with phi-29 DNA polymerase, S1 nuclease and a DNA polymerase having a 5' exonuclease activity.

2. The method of claim 1, wherein said nucleic acid sequence is genomic DNA.

3. The method of claim 1, wherein said single cell is a bacterial cell.

4. The method of claim 1, wherein said amplifying is by multiple displacement amplification.

5. The method of claim 1, wherein said contacting occurs in the following order:
   a) contacting said amplified nucleic acid sequence with phi-29 DNA polymerase;
   b) contacting said amplified nucleic acid sequence with S1 nuclease; and
   c) contacting said amplified nucleic acid sequence with a DNA polymerase having a 5' exonuclease activity.

6. A method of reducing hyperbranched nucleic acid sequences in an amplified nucleic acid sequence from a single cell comprising:
   amplifying a nucleic acid sequence from the single cell to produce an amplified nucleic acid sequence; and
   contacting said amplified nucleic acid sequence with phi-29 DNA polymerase, S1 nuclease and a DNA polymerase having a 5' exonuclease activity to reduce hyperbranched nucleic acid sequences in the amplified nucleic acid sequence,
   such that the amount of hyperbranched nucleic acid sequences in the amplified nucleic acid sequence after contacting is reduced relative to the amount of hyperbranched nucleic acid sequences in the amplified nucleic acid sequence before contacting.

7. The method of claim 6, wherein said nucleic acid sequence is genomic DNA.

8. The method of claim 6, wherein said amplifying is by multiple displacement amplification.

9. The method of claim 6, wherein said single cell is a prokaryotic cell or a eukaryotic cell.

10. The method of claim 9, wherein said prokaryotic cell is a bacterial cell.

11. The method of claim 9, wherein said eukaryotic cell is selected from the group consisting of a yeast cell, an insect cell and a mammalian cell.

12. A method of reducing an amount of chimeric nucleic acid sequences present in cloned DNA comprising:
   amplifying a nucleic acid sequence to produce an amplified nucleic acid sequence;
   contacting said amplified nucleic acid sequence with phi-29 DNA polymerase, S1 nuclease and a DNA polymerase having a 5' exonuclease activity;
   placing said amplified nucleic acid sequence into a vector; and cloning said vector, such that the amount of chimeric nucleic acid sequences present in the amplified nucleic acid sequence after contacting is reduced relative to the amount of chimeric nucleic acid sequences present in the amplified nucleic acid sequence before contacting.

13. The method of claim 12, wherein said nucleic acid sequence that is amplified is genomic DNA.

14. The method of claim 12, wherein said amplifying is by multiple displacement amplification.

15. A method of constructing a genomic library comprising:

obtaining genomic DNA from a single cell;

amplifying said genomic DNA to produce amplified genomic DNA;

contacting said amplified genomic DNA with phi-29 DNA polymerase, S1 nuclease and a DNA polymerase having a 5' exonuclease activity;

placing said amplified genomic DNA into two or more vectors; and transforming each of said vectors into a competent cell.

16. The method of claim 15, wherein said amplifying is by multiple displacement amplification.

17. The method of claim 15, wherein said single cell is a prokaryotic cell or a eukaryotic cell.

18. The method of claim 17, wherein said prokaryotic cell is a bacterial cell.

19. The method of claim 17, wherein said eukaryotic cell is selected from the group consisting of a yeast cell, an insect cell and a mammalian cell.

20. A method of determining genome diversity between two cells comprising:

constructing a first genomic library according to claim 15 for a first cell;

constructing a second genomic library according to claim 15 for a second cell;

sequencing at least a portion of the first genomic library to obtain a first genomic sequence;

sequencing at least a portion of the second genomic library to obtain a second genomic sequence; and comparing the first genomic sequence and the second genomic sequence to determine genome diversity.

21. The method of claim 1 wherein the DNA polymerase is DNA polymerase I.

22. The method of claim 6 wherein the DNA polymerase is DNA polymerase I.

23. The method of claim 12 wherein the DNA polymerase is DNA polymerase I.

24. The method of claim 15 wherein the DNA polymerase is DNA polymerase I.

* * * * *

SEQUENCE LISTING

```
<160> NUMBER OF SEQ ID NOS: 8

<210> SEQ ID NO 1
<211> LENGTH: 19
<212> TYPE: DNA
<213> ORGANISM: Artificial
<220> FEATURE:
<223> OTHER INFORMATION: Synthetic PCR Primer

<400> SEQUENCE: 1
gaagtcgtta ctccaaccc                                                   19

<210> SEQ ID NO 2
<211> LENGTH: 18
<212> TYPE: DNA
<213> ORGANISM: Artificial
<220> FEATURE:
<223> OTHER INFORMATION: Synthetic PCR Primer

<400> SEQUENCE: 2
tcatcgcctc tgtgtgcc                                                    18

<210> SEQ ID NO 3
<211> LENGTH: 20
<212> TYPE: DNA
<213> ORGANISM: Artificial
<220> FEATURE:
<223> OTHER INFORMATION: Synthetic PCR Primer

<400> SEQUENCE: 3
atgcccctac atacccattg                                                  20

<210> SEQ ID NO 4
<211> LENGTH: 22
<212> TYPE: DNA
<213> ORGANISM: Artificial
<220> FEATURE:
<223> OTHER INFORMATION: Synthetic PCR Primer

<400> SEQUENCE: 4
tttttgtcct tgaaacctc ct                                                22
```

```
<210> SEQ ID NO 5
<211> LENGTH: 20
<212> TYPE: DNA
<213> ORGANISM: Artificial
<220> FEATURE:
<223> OTHER INFORMATION: Synthetic PCR Primer

<400> SEQUENCE: 5
tcaagccgga tatcttgtcc                                               20

<210> SEQ ID NO 6
<211> LENGTH: 20
<212> TYPE: DNA
<213> ORGANISM: Artificial
<220> FEATURE:
<223> OTHER INFORMATION: Synthetic PCR Primer

<400> SEQUENCE: 6
attgttattc cgccaccaaa                                               20

<210> SEQ ID NO 7
<211> LENGTH: 18
<212> TYPE: DNA
<213> ORGANISM: Prochlorococcus marinus

<400> SEQUENCE: 7
ttcctaatga aatcatta                                                 18

<210> SEQ ID NO 8
<211> LENGTH: 18
<212> TYPE: DNA
<213> ORGANISM: Prochlorococcus marinus

<400> SEQUENCE: 8
ttcctaatat ttttatta                                                 18
```